(12) United States Patent
Duffy

(10) Patent No.: US 7,244,598 B2
(45) Date of Patent: Jul. 17, 2007

(54) BIOMOLECULE ARRAYS

(75) Inventor: David Duffy, Cambridge, MA (US)

(73) Assignee: Surface Logix, Inc., Brighton, MA (US)

( * ) Notice: Subject to any disclaimer, the term of this patent is extended or adjusted under 35 U.S.C. 154(b) by 0 days.

(21) Appl. No.: 09/928,367

(22) Filed: Aug. 14, 2001

(65) Prior Publication Data

US 2002/0028463 A1  Mar. 7, 2002

Related U.S. Application Data

(60) Provisional application No. 60/225,363, filed on Aug. 14, 2000.

(51) Int. Cl.
C12N 11/04 (2006.01)
Q01N 33/573 (2006.01)
C07H 21/04 (2006.01)

(52) U.S. Cl. .................. 435/182; 435/180; 435/177; 435/176; 435/174; 435/74; 435/71; 435/6; 435/4; 435/DIG. 14

(58) Field of Classification Search ........... 435/7.1, 435/6, 4, 182, 180, 177, 176, 174, 7.4, DIG. 14
See application file for complete search history.

(56) References Cited

U.S. PATENT DOCUMENTS

| 5,569,588 | A | 10/1996 | Ashby et al. |
| 6,197,599 | B1 * | 3/2001 | Chin et al. .................. 436/518 |
| 6,232,066 | B1 * | 5/2001 | Felder et al. .................. 435/6 |
| 6,475,778 | B1 * | 11/2002 | Roberts et al. .......... 435/320.1 |
| 6,485,925 | B1 * | 11/2002 | Duesbery et al. ............. 435/23 |
| 6,488,872 | B1 * | 12/2002 | Beebe et al. ................. 264/31 |
| 6,511,825 | B1 * | 1/2003 | Ruggieri et al. ........... 435/69.1 |
| 6,558,904 | B2 | 5/2003 | Ermantraut et al. |
| 6,630,296 | B2 * | 10/2003 | Xue et al. ....................... 435/4 |
| 6,818,427 | B1 * | 11/2004 | Palombella et al. ........ 435/194 |
| 6,864,224 | B1 * | 3/2005 | Sedivy et al. .................. 512/2 |
| 2001/0053520 | A1 * | 12/2001 | Borrebaeck et al. ........... 435/6 |

FOREIGN PATENT DOCUMENTS

| WO | WO 97/43301 | 11/1997 |
| WO | WO 99/04896 | 2/1999 |
| WO | WO 00/22142 | 4/2000 |
| WO | WO 01/07164 | * 2/2001 |

OTHER PUBLICATIONS

Hui Ge, "UPA, a Universal Protein Array System for Quanitative Detection of Protein-Protein, Protein-DNA, Protein-RNA, and Protein-Ligand Interactions", Nucleic Acids Res. 28(2): e3, (Jan. 2, 2000).

Mere et al, "Minitiurized FRET Assays and Microfluids: Key Components for Ultra-High-Throughput Screening", Drug Discovery Today 4(8); 363-369 (1999).

Havlicek et al., "Cytokinin-Derived Cyclin-Dependent Kinase Inhibitors: Synthesis and cdc2 Inhibitory Activity of Olomoucine and Related Compounds", J. Med.Chem. 40: 408-412 (1997).

International Search Report from corresponding PCT/US01/25351.

* cited by examiner

*Primary Examiner*—T. D. Wessendorf
(74) *Attorney, Agent, or Firm*—Kenyon & Kenyon LLP

(57) ABSTRACT

Array systems that facilitate the simultaneous monitoring of many interactions between biological molecules and the analysis of cellular protein interactions with high throughput. The present invention provides methods and arrays for analyzing biochemical pathways by forming an array of immobilized biomolecules; exposing the array to biomolecules in solution; and detecting modification of the immobilized biomolecules, modification of the biomolecules in solution, and/or binding of biomolecules in solution to immobilized biomolecules.

6 Claims, 6 Drawing Sheets

FIGURE 2. Self-Assembled Monolayers

BIOMOLECULE ARRAYS

CROSS-REFERENCE TO RELATED APPLICATIONS

This application claims priority to U.S. Provisional Application No. 60/225,363, filed on Aug. 14, 2000 and is incorporated by reference herein.

BACKGROUND OF THE INVENTION

Nearly all biological activity is regulated by the interactions of proteins in cells. Proteins are the catalysts, motion transducers, and signal mediators of cells. They control cell division, cell growth, cell differentiation, cell death, and mediate the responses of cells to their environments. To understand cellular processes, we therefore need to monitor the activity of proteins, and to determine the networks of interactions of proteins within cells.

Researchers believe that upwards of 300,000 proteins are translated from the human genome. For many years biologists have endeavored to understand the interactions between these proteins. In the post-genomic era, when the blue-print for all of these proteins will be available, biologists will, in principle, be able to study many more proteins and their interactions.

In the past, the tools available to biologists have only allowed these interactions to be studied one at a time because of a lack of analytical tools that would allow large numbers of protein interactions to be monitored. A system that allowed massively parallel analyses of protein interactions would be of immense value and would speed the progress of biological discovery.

An understanding of cellular signal transduction at a molecular level will provide great insight into disease. This understanding will lead to more effective diagnostic tools and more rational methods of developing drugs. The starting point to understanding biology at the molecular level has been the effort to identify and sequence all of the genes in several organisms, an approach known as genomics. For example, the human genome project has yielded the sequence of all 100,000 human genes. The enormous amount of molecular information that has been made available from these sequencing efforts has given rise to the field of functional genomics.

Functional genomics relates differences in the state of cells, e.g., diseased vs. not diseased, to differences in the levels of their messenger RNA (mRNA). This approach has allowed the functional relationships between many genes to be elucidated. Perhaps the most successful tool in functional genomics has been the complementary-DNA (cDNA) array, which has been commercialized by companies such as Affymetrix, Incyte Genomics, Gene Logic, Nanogen, and Agilent.

Functional genomics is, however, only the first step in using the sequence of genomes to understand biology. Although functional genomics identifies genes of interest, it does not provide molecular level information on how proteins interact to control cell behavior and physiology. For example, the level of transcribed MRNA is not a reliable way to assess the amount or nature of proteins in a cell. This lack of correlation between mRNA and protein levels is due to many factors, including the expression of more than one protein by a single gene, such as via alternative splicing, and post-translational modifications of proteins, such as phosphorylation, methylation, acetylation, lipidation, farnesylation, and glycosylation. Further, genomics does not provide direct information on the interactions between proteins. This lack of direct information is especially prominent in the area of signal transduction pathways, which are largely governed by post-translational modifications.

Functional proteomics is a burgeoning field in which differences in the state of a cell are related directly to differences in the levels of expressed proteins. The strategies now being used for proteomic analyses—2D gel electrophoresis (2DE) and mass spectroscopy—are not optimized for high throughput. These techniques are also limited in that they are not suitable for use with transmembrane proteins, are technically difficult to perform, and have limited ability to detect low abundance proteins, such as those in signal transduction pathways. A limitation to the use of functional proteomics is that a general and flexible technology, akin to cDNA arrays, that can detect proteins and their interactions is not available currently in proteomics.

Protein arrays provide a general tool that allows biological researchers to perform assays with high throughput. Protein arrays are patterned arrays of known biomolecules that can undergo a molecular recognition with specific proteins amongst a complex mixture of proteins in solution. Various concepts have been proposed for protein arrays. The most common is composed of arrays of monoclonal antibodies that bind to specific proteins in a similar way that arrays of cDNA capture mRNA. Other approaches include the use of arrays of chemicals which bind proteins. Arrays such as these have been used to isolate proteins, but no array system useful for monitoring interactions between proteins yet exists.

There is therefore a need for an array system that provide a flexible and general tool for studying protein-protein interactions with sufficiently high throughput.

SUMMARY OF THE INVENTION

The present invention provides array systems that facilitate the simultaneous monitoring of many interactions between biological molecules. Biomolecule arrays according to the present invention provide a flexible and general tool and will allow biological researchers to probe cellular protein interactions with high throughput.

In certain embodiments, these systems are adapted to be used to investigate the effect of a drug or other substance on a biomolecule or biomolecules. In certain embodiments, the effect(s) of a drug or other substance on a biomolecule or biomolecules of a pathway or pathways is analyzed. In such embodiments, the biomolecules and/or pathway may be known or unknown and characterized or uncharacterized. Likewise, the drug or other substance may be identified or unidentified and may be characterized or uncharacterized.

In one embodiment, these systems are adapted to be used to elucidate signal transduction pathways and other biological processes governed by enzyme-mediated, post-translational modifications. In certain embodiments, the array systems of the present invention are adapted to facilitate the performance of assays with high throughput. Methods for preparing and using array systems according to the present invention are provided.

As used herein, the terms "biological molecules" and "biomolecules" may be used interchangeably. These terms are meant to be interpreted broadly, and generally encompass organic molecules that are produced by biological systems or other biological molecules, organic molecules that are capable of affecting or altering biological systems when placed in contact therewith, and organic molecules capable of modifying or binding to other biological molecules. "Biological systems" should likewise be interpreted broadly to encompass, for example, organisms, organ systems, organs, tissues, cells, and biological molecules that interact in vitro. The term "biomolecules" also includes inorganic molecules that are produced by biological systems or other biological molecules, inorganic molecules that are capable of affecting or altering biological systems when placed in contact therewith, and inorganic molecules capable of modifying or binding to other biological molecules. For example, inorganic vitamins, minerals, toxins, drugs, and cofactors may be encompassed by the term "biomolecules" as used herein.

As non-limiting examples, biomolecules include oligosaccharides, polysaccharides, oligopeptides, polypeptides, peptides, proteins, oligonucleotides, and polynucleotides. Oligonucleotides and polynucleotides include, for example, DNA and RNA. Biomolecules also include organic compounds, organometallic compounds, salts of organic and organometallic compounds, saccharides, amino acids, and nucleotides, lipids, carbohydrates, drugs, toxins, venoms, steroids, lectins, vitamins, minerals, metabolites, cofactors, and coenzymes. The term "drugs," as used herein, should be interpreted broadly to include drugs of known efficacy and safety, drug candidates picked randomly from libraries of biomolecules, and drugs at every level of investigation therebetween.

Biomolecules further include derivatives of the molecules described. For example, derivatives of biomolecules include lipid and glycosylation derivatives of oligopeptides, polypeptides, peptides, and proteins. Further examples of derivatives of biomolecules include lipid derivatives of oligosaccharides and polysaccharides, e.g., lipopolysaccharides.

Biomolecules may be considered as groups, or classes, of differing degrees of inclusivity. For example, proteins and lipids may be considered to be two different classes of biomolecule. Being more exclusive, enzymes and structural proteins are examples of two classes of protein. More exclusively still, peptidases and kinases are examples of two classes of enzymes. As use herein, any of these degrees of grouping may be referred to as classes of biomolecules. As used herein, a "type" of biomolecule refers to a specific biomolecule. For example, protein kinase A is one type of biomolecule. Likewise, protein kinase C is another type of biomolecule. Arrays according to the present invention may comprise one or more type of biomolecule, and different types of biomolecule may be from the same or different class of biomolecules.

In certain embodiments, array systems according to the present invention comprise biomolecules immobilized on a surface. In certain embodiments, the surface may be activated, adapted, prepared, or modified to facilitate the binding of biomolecules.

The term "array," as used herein, generally refers to a predetermined spatial arrangement of binding islands, biomolecules, or spatial arrangements of binding islands or biomolecules. Array systems according to the present invention that comprise biomolecules immobilized on a surface may also be referred to as "biomolecule arrays." Array systems according to the present invention that comprise surfaces activated, adapted, prepared, or modified to facilitate the binding of biomolecules to the surface may also be referred to as "binding arrays." Further, the term "array" may be used herein to refer to multiple arrays arranged on a surface, such as would be the case where a surface bore multiple copies of an array. Such surfaces bearing multiple arrays may also be referred to as "multiple arrays" or "repeating arrays." The use of the term "array" herein may encompass biomolecule arrays, binding arrays, multiple arrays, and any combination thereof; the appropriate meaning will be apparent from context.

Surfaces useful according to the present invention may be of any desired shape (form) and size. Non-limiting examples of surfaces include chips, continuous surfaces, curved surfaces, flexible surfaces, films, plates, sheets, tubes, and the like. Surfaces preferably have areas ranging from approximately a square micron to approximately 500 cm$^2$. The area, length, and width of surfaces according to the present invention may be varied according to the requirements of the assay to be performed. Considerations may include, for example, ease of handling, limitations of the material(s) of which the surface is formed, requirements of detection systems, requirements of deposition systems (e.g., arrayers), and the like. In certain embodiments, surfaces are approximately 106 cm$^2$. In certain embodiments, surfaces have a length and width similar to the length and width of a standard 96 (or 384, 1536, or 3456) well plate.

Surfaces useful according to the present invention may be of any suitable thickness. The thickness of surfaces according to the present invention may be varied according to the requirements of the assay to be performed. Considerations may include, for example, ease of handling, limitations of the material(s) of which the surface is formed, requirements of detection systems, requirements of deposition systems (e.g., arrayers), and the like. For example, where SPR will be used for detection, the surface will ordinarily preferably be 30 or fewer nanometers thick. Surfaces to be read with fluorescent plate readers may be thicker, such as approximately 1 cm thick. Typically, the surface may have a thickness of between approximately 50μ to approximately 2 cm.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within wells of 96, 384, 1536, or 3456 microwell plates. In such embodiments, the bottoms of the wells may serve as surfaces for the formation of arrays, or arrays may be formed on other surfaces then placed into wells. In certain embodiments, such where a surface without wells is used, binding islands may be formed or biomolecules may be immobilized on a surface and a gasket or contact mask, having holes spatially arranged so that they correspond to the islands or biomolecules may be placed on the surface. Such a gasket or contact mask is preferably liquid tight. A gasket, or contact mask, may be placed on a surface at any time during the process of making the array and may be removed if separation of groups or arrays is no longer necessary. See, e.g., co-pending U.S. Ser. No. 09/705,187, entitled Polymer Gel Contact Masks And Methods And Molds For Making Same. Specifically, a contact mask is placed over a substrate to conceal a portion of the substrate and leave a plurality of discontinuous portions of the substrate exposed. Such a mask has a plurality of holes through it. Each of the holes, together with the portion of the substrate surface which it overlies, forms a cavity. Biological and chemical materials can be deposited into each of the cavities individually. The polymer gel contact masks are gel forming polymers that do not dissolve in liquids with which they form gels because the polymer chains are bound together, such as by covalent bonds as in crosslinking or by extensive physical interactions as in interpenetrating polymer networks. Gel-forming polymers typically are crosslinked polymer networks. Crosslinking between the chains prevents separation of the polymer chains from each other which would lead to dissolution. Preferred gel-formed polymers are hydrogels. The hydrogels are especially well suited for use as contact masks in the patterning of biological materials upon a substrate.

Contact masks are articles elongated in two dimensions relative to the third dimension. Accordingly, they have expansive bottom and top surfaces compared to the side surfaces. Contact masks for patterning biological materials typically have one or more holes extending from the top surface to the bottom surface.

In certain embodiments, biomolecules are immobilized in discrete areas. Preferably, such discrete areas are surrounded by areas to which substantially no biomolecules are bound. In certain other embodiments, a surface is adapted, prepared, or modified to facilitate the binding of biomolecules to discrete areas of the surface. Areas which are modified to facilitate the binding of biomolecules may be referred to herein as "binding islands" or "binding areas." Preferably, binding areas are surrounded and separated from each other by regions which do not bind, or which resist binding, biomolecules.

In some embodiments, immobilized biomolecules bind biomolecules from a solution overlying the immobilized biomolecules. In other embodiments, immobilized biomolecules modify or are modified by biomolecules in a solution overlying the immobilized biomolecules. In other embodiments, array systems of the present invention mimic signal transduction processes that occur in cells. In still other embodiments, array systems of the present invention are adapted for the investigation of the activity of enzymes, (such as, but not limited to, kinases) that are involved in signal transduction pathways. In yet other embodiments, array systems of the present invention are adapted for the investigation of interactions of biomolecules in solution with numerous members of a particular class of biomolecules. In certain embodiments, array systems of the present invention provide greater biochemical information compared to a conventional protein chip.

According to certain embodiments of the present invention, biomolecules are immobilized on a surface or surfaces to form an array. Biomolecules may be immobilized on a surface through the use of intermediary molecules that are capable of binding biomolecules. These intermediary molecules may also be referred to herein as "affinity molecules." Such intermediary molecules are bound to or layered over a surface, and biomolecules are immobilized to the intermediary molecules. Biomolecules that are immobilized on a surface through the use of intermediary molecules are encompassed by the term "biomolecules immobilized on a surface." Likewise, references to immobilization of biomolecules on a surface may refer to immobilization directly onto the surface or to immobilization via the use of intermediary molecules, and the appropriate meaning will be evident from context.

One or more types or classes of biomolecules may be immobilized on a single surface. In certain embodiments, biomolecules of many different types or classes, e.g., 1000's, are immobilized. In other embodiments, biomolecules of fewer types or classes, e.g., 100's, are immobilized. In other embodiments, biomolecules of fewer types or classes, e.g., 100 or fewer, are immobilized. In yet other embodiments, biomolecules of even fewer types or classes, e.g., from 1 to 99, are immobilized. The number of classes or types of biomolecules immobilized on a particular array according to the present invention may be chosen based on such factors as the assay(s) to be performed, the size of the biomolecules, the desired distance between the biomolecules, and the like.

According to certain embodiments of the present invention, one or more surfaces are modified, adapted, or prepared to facilitate the binding of biomolecules to the surface. Such preparation may comprise the immobilization or layering onto the surface molecules capable of binding other molecules. Molecules capable of binding other biomolecules may be referred to herein as "affinity molecules." Affinity molecules include molecules capable of binding biomolecules and molecules capable of binding to specific binding groups attached to biomolecules. Such binding groups may be attached to biomolecules through any suitable means: for example, they may be a naturally-occurring part of a biomolecule, they may be attached chemically, biomolecules bearing the groups may be produced using recombinant DNA technology, or they may be attached to biomolecules in disease processes or in response to exposure to environmental stress, drugs, toxins, and the like. Affinity molecules may bind to biomolecules in general, or they may be specific for one or more class of biomolecules or binding groups. Affinity molecules may be still more specific: they may bind to only a few types or a single type of biomolecule or binding group.

A surface may be prepared so that one or more types or classes of biomolecules may be immobilized on a single surface. In certain embodiments, a surface may be prepared so that biomolecules of many different types or classes, e.g., 1000's, may be immobilized on that surface. In other embodiments, a surface may be prepared so that biomolecules of fewer types or classes, e.g., 100's, may be immobilized on that surface. In other embodiments, a surface may be prepared so that biomolecules of fewer types or classes, e.g., 100 or fewer, may be immobilized on that surface. In yet other embodiments, a surface may be prepared so that biomolecules of even fewer types or classes, e.g., from 1 to 99, may be immobilized on that surface. The number of classes or types of biomolecules for which a particular array according to the present invention is prepared may be chosen based on such factors as the assay(s) to be performed, the size of the biomolecules, the desired distance between the biomolecules, and the like.

In some embodiments, biomolecules are immobilized on a surface in patterns, or arrays. In other embodiments, surfaces are modified, adapted, or prepared so that biomolecules may be immobilized thereon in patterns, or arrays.

In certain embodiments, biomolecules are immobilized using methods and materials that minimize alterations in the nature of the biomolecules, or that minimize interactions between the biomolecules and the surface on which they are immobilized. In certain such embodiments, the immobilization is accomplished by forming one or more self-assembling monolayers (SAMs) on the surface and immobilizing biomolecules on some or all of the SAMs.

Immobilized biomolecules may be derived from any source of interest. In certain embodiments, biomolecules to be immobilized are or are derived from a supernatant of a cell culture. The cells in culture may be derived from any source of interest. In certain other embodiments, biomolecules to be immobilized are or are derived from a cell lysate. The cell lysate may be derived from any source of interest. Non-limiting examples of such sources include cells in culture, immortalized cell lines, and cells, tissues, or organs taken directly from a living or dead organism. In other embodiments, biomolecules to be immobilized are or are derived from a fluid or fluids taken from a living or dead organism. Non-limiting examples of such fluids include blood, tears, saliva, gastrointestinal fluid, amniotic fluid, bone marrow, plasma, lymph, extracellular fluids, sap, cerebrospinal fluid, and urine. Such fluids may be referred to herein as "physiological fluids." In yet other embodiments, biomolecules to be immobilized are or are derived from a protein or peptide library or other library. In certain embodiments, biomolecules to be immobilized comprise drugs or drug candidates. Samples comprising biomolecules other than biomolecules of interest may be fractionated, thereby reducing or eliminating biomolecules not of interest, before being applied to binding islands of the present invention. However, in certain embodiments of the present invention, such fractionation is unnecessary because the binding islands exhibit binding specificity for certain types or classes of biomolecules.

In many embodiments, immobilized biomolecules, or biomolecules to be immobilized, are proteins. One or more types of proteins may be immobilized on a surface. In certain embodiments, the proteins are immobilized using methods and materials that minimize the denaturing of the proteins, that minimize alterations in the activity of the proteins, or that minimize interactions between the protein and the surface on which they are immobilized. In certain embodiments, these biomolecules are proteins involved in pathways that are important in signal transduction.

Surfaces bearing immobilized biomolecules may be exposed to solutions comprising biomolecules which bind to, modify, or are modified by the biomolecules immobilized on the surface. Such surfaces may be referred to as "solutions of interest." In certain embodiments, one or more type or class of biomolecules of interest is suspended in a solution. In certain embodiments, the solution is or is derived from a supernatant of a cell culture. The cells in culture may be derived from any source of interest. In certain other embodiments, the solution is or is derived from a cell lysate. The cell lysate may be derived from any source of interest. Non-limiting examples of such sources include cells in culture, immortalized cell lines, and cells, tissues, or organs taken directly from a living or dead organism. In other embodiments, the solution is or is derived from a fluid or fluids taken from a living or dead organism. Non-limiting examples of such fluids include blood, tears, saliva, gastrointestinal fluids, amniotic fluid, bone marrow, plasma, lymph, extracellular fluids, sap, cerebrospinal fluid, and urine. Such fluids may be referred to herein as "physiological fluids." In yet other embodiments, the solution is or is derived from a protein or peptide library or other library. In certain embodiments, the solution to which arrays according to the present invention are exposed comprise drugs or drug candidates.

In certain embodiments, immobilized biomolecules and/or biomolecules in solution comprise biomolecules that are members of biochemical pathways. A biochemical pathway, which may be referred to herein as simply a "pathway", comprises sequential collection of processes or reactions a cell uses to transmit stimuli. Such stimuli may be, for example, external stimuli transmitted into the cell into the inside a cell. As another non-limiting example, such stimuli may be cytosolic stimuli transmitted into the nucleus. Each of processes or reactions usually involve a series of interactions between two or more biomolecules. For example, one biomolecule may modify the other, such that the modified biomolecule is, for example, activated or inactivated. Biomolecules involved in a given pathway may be referred to as "members" of that pathway.

Where reference is made herein to interaction between immobilized biomolecules and a solution of interest, it will be appreciated that the interaction is between biomolecules in the solution and immobilized biomolecules. Where reference is made herein to the detection of an interaction between biomolecules, it will be appreciated that the binding of biomolecules to one another or modifications to one or more of the biomolecules that interact are detected; "interaction" between biomolecules may be used herein as a shorthand for binding together of one or more biomolecules and to modifications to one or more of the interacting biomolecules as a result of that interaction. Non-limiting examples of modifications include chemical, structural, and physical modifications. Further, reference is made herein to exposure of immobilized biomolecules to solutions of interest and to exposure of solutions of interest to immobilized biomolecules. Unless explicitly stated otherwise, these two references are simply different ways of phrasing one concept—that of putting immobilized biomolecules and solutions of interest in contact with one another.

As used herein, the term "solution" includes any media in which molecules are not bound to a substrate that is fixed in position in relation to biomolecules immobilized on surfaces according to the present invention. Non-limiting examples of solutions include liquids, emulsions, suspensions, gels, foams, and the like.

Proteins, other biomolecules, cell lines, cells, physiological fluids, and libraries which may be studied using arrays according to the present invention may be derived from sources that include, but are not limited to animals, plants, algae, fungi, bacteria, viruses, protazoa, and any other life form of interest. Arrays according to the present invention are also useful for studying proteins and other biomolecules produced via chemical synthesis, enzymatic synthesis, recombinant nucleotide technology, and other in vitro methods. In embodiments in which the solution is or is derived from a fluid, culture supernatant, library, or cell lysate, the solution may be an entire library or unaltered cell lysate, culture supernatant, or fluid; or the library, lysate, supernatant, or fluid may be subjected to other methods of separation, fractionation, or characterization, to produce a solution to which an array will be exposed.

In certain embodiments, cells are treated with drugs or drug candidates of interest, then the cells are lysed and arrays according to the present invention are exposed to the cell lysate. In other embodiments, cells are cultured in miniaturized microfluidic systems that are integrated with arrays according to the present invention. Products released by and/or lysates of cells so cultured may then be analyzed on arrays integrated with the cell culturing system itself. Cells may be cultured, lysed, and exposed to arrays without needing to relocate the cells.

Binding between biomolecules in solution and immobilized biomolecules and/or modifications to biomolecules in solution and/or modifications to immobilized biomolecules are detected using detection techniques known in the art. In certain embodiments, antibodies reactive with a biomolecule having a particular modification, but not reactive with non-modified biomolecules or biomolecules having other modifications, are used to detect particular modifications. Binding of one or more different antibodies to their specific targets may be assessed. In embodiments in which binding to more than one antibody is assessed in a single assay, different antibodies may be differentially labeled. However, differential labeling is not necessary, as the antibodies may also be distinguished on the basis of the position of the immobilized biomolecules to which they bind. Labeling of antibodies is well-known in the art. The use of primary antibodies, which bind molecules of interest, and secondary antibodies, which are labeled and which bind the primary antibodies is an example of a detection technique useful in the practice of the present invention. As non-limiting examples, antibodies may be radiolabeled or labeled with fluorescent tags. In other embodiments, mass spectroscopy is used to differentiate between modified and non-modified biomolecules. In still other embodiments, surface plasmon resonance is used to differentiate between modified and non-modified biomolecules. Other detection systems are known in the art.

The array systems of the present invention can be used to elucidate interactions between molecules. For example, methods and arrays according to the present invention may be used to determine the effects of enzymes upon biomolecules, and may also be used to identify and/or characterize inhibitors of enzymes. In an even more specific example, the biomolecules in solution and biomolecules immobilized on an array may be selected so that the system mimics signal transduction pathways, facilitating the characterization of enzymes, such as kinases, enzyme substrates, enzyme inhibitors, and other molecules of interest. As another example, methods and arrays according to the present invention may be used to determine the effects of biomolecules such as drugs and toxins on organisms, organs, tissues, cells, pathways, and individual biomolecules. As yet another example, methods and arrays according to the present invention may be used to elucidate drug-drug interactions.

As will be further explained herein, the array system according to the present invention provides for high throughput, as many interactions may be tested in a single assay. Likewise, array systems according to the present invention facilitate the simultaneous study of different pathways. Arrays according to the present invention are especially useful in the simultaneous study of interconnected or overlapping pathways. In certain embodiments, arrays according to the present invention facilitate the simultaneous study of unrelated pathways. As a non-limiting example, biomolecules from one pathway may be arrayed on a surface, biomolecules from another pathway may be arrayed on a different part of the same surface, then the surface may be exposed to, for example, a cell lysate. Thus, in this manner, biomolecules representing two different pathways may be exposed simultaneously to a cell lysate.

Arrays comprising binding islands or areas may be included in kits, and such kits comprise another embodiment of the present invention. Such kits may also include, as non-limiting examples, reagents useful for preparing biomolecules for immobilization onto binding islands or areas of an array according to the present invention, reagents useful for detecting modifications to immobilized biomolecules, or reagents useful for detecting binding of biomolecules from solutions of interest to immobilized biomolecules.

Likewise, arrays comprising immobilized biomolecules may be included in kits, and such kits comprise yet another embodiment of the present invention. Such kits may also include, as non-limiting examples, reagents useful for detecting modifications to immobilized biomolecules or for detecting binding of biomolecules from solutions of interest to immobilized biomolecules.

DETAILED DESCRIPTION

Figure 1:
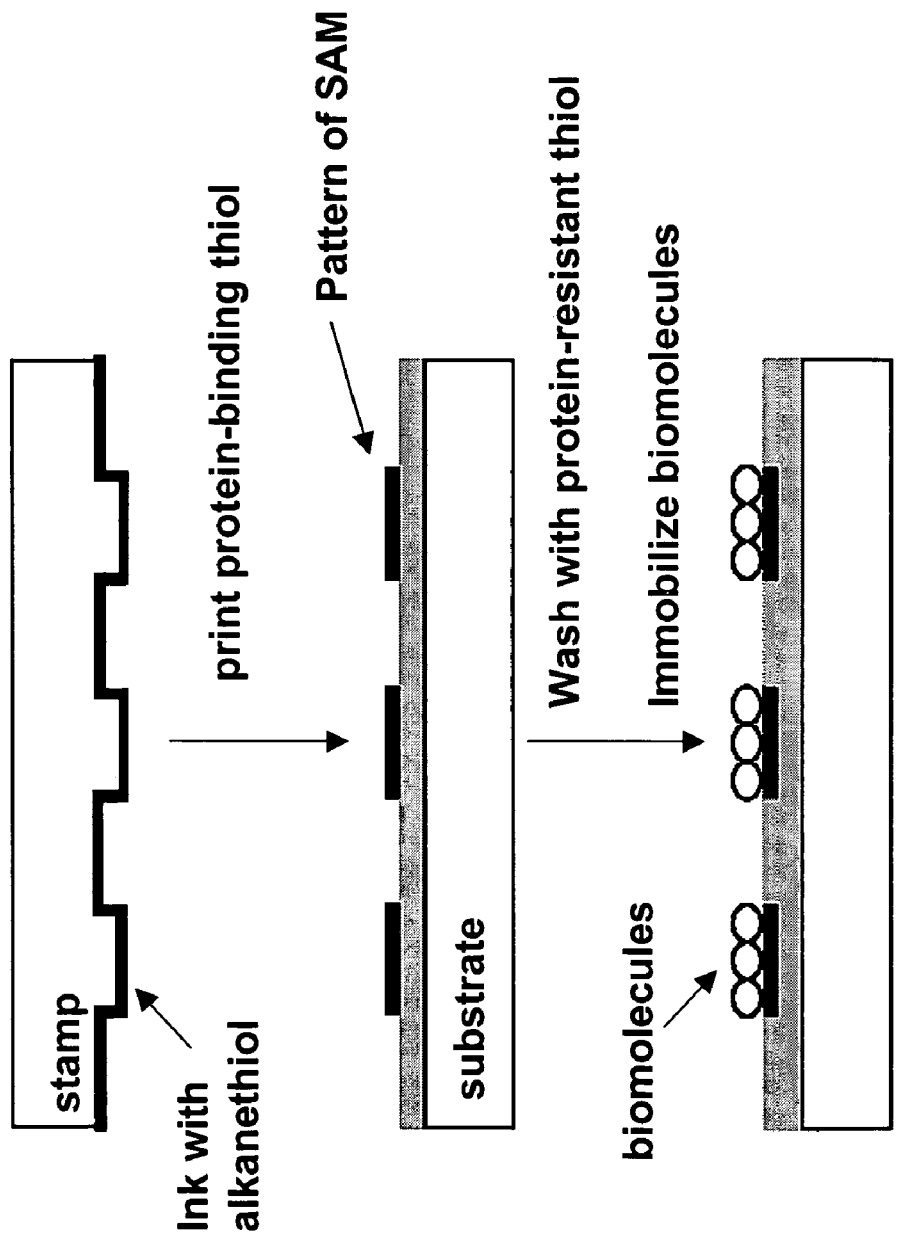
FIG. 1 is a schematic representation of method for constructing a biomolecule array using microcontact printing of alkanethiols onto a gold surface. The pattern of the array is a function of the relief structure on the stamp used for printing.

According to certain embodiments of the present invention, biomolecules are immobilized on surfaces. Preferably, biomolecules are immobilized so that they form patterns, or arrays. In preferred embodiments, immobilized biomolecules are arranged in a pattern comprising discrete spots, or islands, of biomolecules surrounded by areas having substantially no biomolecules immobilized thereon. In alternative embodiments, discrete islands having biomolecules immobilized thereon may be immediately adjacent to areas having different biomolecules immobilized thereon.

Surfaces that have been modified, adapted, or prepared in order to facilitate immobilization of biomolecules thereon, but which do not yet have biomolecules immobilized thereon, comprise another embodiment of the present invention. Such prepared surfaces may also be an intermediary step in the production of surfaces bearing immobilized biomolecules. Preferably, surfaces are prepared so that biomolecules may be immobilized thereon so that the biomolecules form patterns, or arrays. In preferred embodiments, surfaces are prepared such that biomolecules may be immobilized so that they form a pattern comprising discrete spots, or islands, of biomolecules surrounded by areas having substantially no biomolecules immobilized thereon. In alternative embodiments, surfaces are prepared such that, after biomolecules of interest are immobilized thereon, the surface comprises discrete islands having biomolecules immobilized thereon which are immediately adjacent to areas having different biomolecules immobilized thereon.

An island or area to which biomolecules may be bound may be referred to herein as a "binding island" or "binding area." It may be said that binding islands or areas are "capable of" binding biomolecules thereon. In other words, binding islands or areas will bind biomolecules if they are exposed thereto or may be modified so that they will bind biomolecules if exposed thereto. When used without the phrase "capable of," the terms "binding island" and "binding area" may refer to areas having biomolecules bound thereto, to areas capable of having biomolecules bound thereto, or to both. The meaning of "binding area" and "binding island" will be apparent in context. Binding areas or islands may have different binding specificities. Therefore, an island or area need not be capable of binding all biomolecules in order to be considered to be a binding island or area. For example, a given binding island may be specific for binding a certain class or type of biomolecule.

Biomolecules may be bound directly to a surface, but are preferably bound to intermediary molecules which bind biomolecules and which are immobilized on or form a layer on the surface. Such intermediary molecules are bound to or layered over a surface, and biomolecules are immobilized to the intermediary molecules. For example, as will be elaborated herein, a SAM (self assembling monolayer) may be formed on a surface, and the SAM may comprise SAM-forming molecules (SFMs) that bind biomolecules. An area of a SAM that binds biomolecules may be referred to as a "binding island" or a "binding area."

Biomolecules that are immobilized on a surface through the use of intermediary molecules are encompassed by the term "biomolecules immobilized on a surface." Likewise, references to immobilization of biomolecules on a surface may refer to immobilization directly onto the surface or to immobilization via the use of intermediary molecules, and the appropriate meaning will be evident from context.

Any given binding island may be prepared such that a single or multiple copies of one type of biomolecule may be immobilized on that island. In many embodiments, binding islands will be prepared so that a discrete island will be capable of binding thereon one type or class of biomolecule and a second discreet island will be capable of binding thereon a different type or class of biomolecule. Additional discreet islands that are capable of binding thereon yet other different types or classes of biomolecules may also be included on a surface. Of course, a single island may be prepared so that it is capable of binding thereon different types or classes of biomolecules.

Preferably, the diameter of binding islands or areas according to the present invention is 100 microns or fewer. More preferably, the diameter of binding islands or areas according to the present invention is 50 microns or fewer. Even more preferably, the diameter of binding islands or areas according to the present invention is 20 microns or fewer. Most preferably, the diameter of binding islands or areas according to the present invention is 5 microns or fewer. Preferably, arrays according to the present invention have from 0 to 100 microns of non-binding area between binding islands. More preferably, from 30 to 60 microns of non-binding area lies between binding islands. Sizes of binding islands and non-binding areas may be chosen according to such considerations as the number of islands desired, the area of the surface, the desired configuration of the islands, and the desired proximity of the immobilized biomolecules.

Multiple islands of molecules having dimensions as described may be arranged in arrays. Such arrays may be arranged in the wells of 96, 384, 1536, or 3456 well microwell plates or in areas the size and orientation of the wells of a 96, 384. 1536, or 3456 microwell plate. Due to the extremely small diameter of the binding islands, many binding islands may be placed within each microwell. As an example, an array comprising binding islands having a diameter of 100 microns each and separated by non-binding areas of approximately 0 to 60 microns would allow for the placement of approximately 500 binding islands in an area the size of single well of a 96 well plate (each well has a diameter of approximately 5 mm). As another example, an array comprising binding islands having a diameter of 20 microns each and separated by non-binding areas of approximately 0 to 60 microns would allow for the placement of approximately 14,000 binding islands in an area the size of a single well of a 96 well plate.

As is discussed further herein, deposition of molecules in islands of such sizes may be accomplished through the use of soft lithographic techniques. For example, a mask having apertures of the desired sizes may be used to deposit molecules in islands of the desired sizes. In certain embodiments, other techniques, such as, but not limited to washing, dripping, spraying, dipping, and the use of arrayers are useful in the fabrication and use of arrays according to the present invention.

A single or multiple copies of one type of biomolecule may be immobilized on any given island. In many embodiments, a discrete island will have immobilized thereon one type or class of biomolecule and a second discreet island will have immobilized thereon a different type or class of biomolecule. Additional discreet islands may have immobilized thereon yet other different types or classes of biomolecules. Of course, more than one discreet island may have the same type or class of biomolecule immobilized thereon. Likewise, a single discreet island may have immobilized thereon different types or classes of biomolecules.

Preferably, the diameter of islands of biomolecules according to the present invention is 100 microns or fewer. More preferably, the diameter of islands of biomolecules according to the present invention is 50 microns or fewer. Even more preferably, the diameter of islands of biomolecules according to the present invention is 20 microns or fewer. Most preferably, the diameter of islands of biomolecules according to the present invention is 5 microns or fewer. Deposition of biomolecules in islands of such sizes may be accomplished through the use of soft lithographic techniques. For example, a mask having apertures of the desired sizes may be used to deposit biomolecules in islands of the desired sizes. Multiple islands of biomolecules having dimensions as described may be arranged in arrays. Such arrays may be arranged in any suitable configuration. Configurations of binding islands and non-binding areas may be chosen according to such considerations as the number of islands desired, the area of the surface, the size of the islands, and the desired proximity of the immobilized biomolecules. For example, such arrays may be formed on surfaces in a larger pattern similar in shape and size to wells of a 96, 384, 1536, or 3456 well plate. As another example, arrays may be arranged on the bottom surface of wells of 96, 384, 1536, or 3456 well microwell plates.

Preferably, the surfaces on which biomolecules are immobilized are formed of materials that are inert and/or are capable of resisting the adsorption of biomolecules, such as proteins, by non-specific reactions. The use of materials which do not readily adsorb biomolecules is preferable because non-specific adsorption could cause a molecule to be adsorbed at more than one site, which could alter the characteristics of the molecule. In the case of proteins, non-specific adsorption would likely cause proteins immobilized on the surface to unfold and denature, thus reducing, altering, eliminating their activity. Non-specific adsorption of biomolecules to the surface would also greatly hamper the ability to immobilize specific biomolecules of interest and/or to immobilize biomolecules in specific locations. The use of a surface to which biomolecules are less likely to attach, as opposed to a surface which biomolecules are very likely to attach, is preferred.

Further, as will be explained further herein, all or portions of non-inert surfaces (surfaces to which biomolecules attach to some degree) may be rendered inert by forming inert SAMs on the areas of the surfaces desired to be inert. Inert surfaces include those surfaces to which substantially no biomolecules attach.

As used herein, "substantially no" attachment indicates a level of non-specific or undesired attachment of biomolecules which does not prevent detection of interactions sought to be investigated. In other words, "substantially no" non-specific binding occurs when the signal to noise ratio for interactions sought to be detected remains at or above a value detectable by the detection systems being employed. Thus, the definition of "substantially no" varies with such factors as the resolving power of the array and the detection method employed. The definition of "substantially no" for a given system may be determined empirically with routine experimentation. For example, a surface may be tested for binding by incubating it with a solution of biomolecules. The level of binding may be measured. As another example, a surface bearing areas (e.g., of SAMs) intended to be binding islands and areas (e.g., of SAMs) intended to be non-binding areas may be incubated with a solution of biomolecules. The ratio of the number of molecules bound in areas intended to be binding islands compared to the number of molecules bound in areas intended to be inert can be measured. Such control experiments can be performed for different types of binding molecules, and for different detection systems, all without undue experimentation. See, e.g., Mrksich M., et al., *Annu Rev Biophys Biomol Struct* 25: 55–78 (1996).

Examples of materials useful in forming surfaces for forming arrays according to the present invention include gold, silver, platinum, palladium, and copper. Other examples of materials useful in forming surfaces for forming arrays according to the present invention include glass, silicon, ceramics, and plastics.

Most preferably, the surfaces are formed of gold or are gold-coated. For example, silicon wafers coated with gold are useful as surfaces in certain embodiments of the present invention.

Biomolecules may be immobilized on the surfaces by any suitable method known in the art. Preferably, the immobilization is performed using techniques which do not damage biological molecules. For example, the use of UV light and organic solvents in a manner that damages biological molecules is preferably avoided.

Exemplary methods of immobilizing biomolecules are known in the art. Such methods include affinity capture, covalent derivatization, such as with EDC+NHS, direct coupling, and membrane anchoring, the use of streptavidin-biotin, nickel chelation capture, and the like.

Preferably, preparing a surface for immobilization of biomolecules thereon in order to produce arrays according to the present invention is accomplished via forming a SAM on the surface. Even more preferably, one or more types of SAM-forming molecules (SFMs) is engineered to form a pattern on the surface. Most preferably, soft lithographic application of SAM-forming molecules (SFMs) is used to form a patterned monolayer on the surface. As is further explained herein, types of SFMs useful for creating arrays in accordance with the present invention include, but are not limited to, SFMs that do not bind to biological molecules and SFMs that bind specifically to a particular biomolecule or type of biomolecule.

Arrays according to the present invention include surfaces having a SAM or SAMs having biomolecules immobilized thereon in at least one area. Arrays according to the present invention also include surfaces having a SAM or SAMs immobilized thereon, which SAM or SAMs comprise at least one area wherein at least some of the SFMs forming the SAM are capable of binding biomolecules.

Any suitable method may be used to expose a surface or molecules bound to or formed on a surface, such as a SAM, to other molecules, such as biomolecules, sought to be immobilized on the surface. Non-limiting examples of suitable methods include soft lithography, washing, dripping, spraying, dipping, microfluidic delivery, and deposition with an arrayer. Techniques such as these are useful at many stages in the process of fabrication of arrays according to the present invention. As non-limiting examples, such techniques may be used to deposit molecules directly onto a surface. Molecules which may be deposited include biomolecules, molecules capable of binding biomolecules, and molecules that resist binding to or do not bind to biomolecules. As another example, such techniques are useful for exposing molecules, such as SFMs forming a SAM, layered on or bound to a surface to other molecules, such as biomolecules desired to be immobilized to the molecules bound or layered on the surface. As yet another example, these techniques are useful for exposing immobilized biomolecules to solutions of interest.

Arrayers are well known in the arts of genomics and arrays. Generally, these machines remove samples from a 96 or 384 micro-well plate then deposit the samples onto a substrate, or surface, or into wells of another micro-well plate, while maintaining the spatial orientation and separation between samples. Exemplary arrayers include the Biomek 2000 from Beckman Instruments and the Omnigrid from GeneMachines. Arrayers may be used, for example, to transfer proteins from a library of proteins to binding islands of an array according to the present invention. For instance, using arrayer technology (as described herein and as known in the art), it is possible to transfer a different type of SFC to each of 500 spots in a given well of a 96 well plate (or in an area the size of such a well on a substrate) to form 500 binding islands and to predetermine the location of each type of binding island in the array of 500 islands. If desired, this procedure can be repeated for each of the 96 wells in a 96 well plate (or for each of 96 areas the size and spatial orientation of such wells on a substrate), thereby producing 96 duplicate arrays of 500 different types of binding island each in a predetermined spatial orientation. Similar methods may be used to create arrays of 14,000 types of biomolecules in 384 well plates or on substrates.

Likewise, using arrayer technology (as described herein and as known in the art), it is possible to transfer a different type of biomolecule to each of 500 binding islands in a given well of a 96 well plate (or in an area the size of such a well on a substrate) and to predetermine the location of each type of biomolecule in the array of 500 islands. If desired, this procedure can be repeated for each of the 96 wells in a 96 well plate (or for each of 96 areas the size and spatial orientation of such wells on a substrate), thereby producing 96 duplicate arrays of 500 different types of protein each in a predetermined spatial orientation. Similar methods may be used to create arrays of 14,000 types of biomolecules in 384 well plates or on substrates.

Soft lithography is a set of fabrication techniques that have been developed as alternatives to photolithography and which are particularly useful for patterning on a microscopic level. Soft lithography has been used to fabricate or replicate patterns of biological materials with feature sizes that range from approximately 1 micron to approximately 1 mm. Soft lithography is also ideally suited to patterning arrays of biological material and is directly compatible with SAM technology. Soft lithography's biocompatibility derives from the fact that the techniques may be performed without the use of organic solvents or UV light, which are harmful to many biological materials.

Compared to conventional microfabrication techniques, soft lithography techniques require little capital investment and utilize materials which are themselves of low cost. Further, as explained below, soft lithography enables the integration of protein arrays with current drug discovery systems. Any suitable soft lithography technique may be used to pattern SAMs according to the present invention.

The common element in soft lithography is a polymer template that contains features to be transferred or replicated. In one embodiment, the pattern transfer element is produced by casting a liquid precursor of polydimethylsiloxane (PDMS) on a master, curing it to solid, and removing if from the master. The PDMS replica can be used as a stamp to transfer chemical "ink", as a stencil mask through which materials are deposited, or as a mold to form topological structures. Micro-contact printing (MCP) is an example of a soft lithographic technique. The use of MCP to form a SAM will be described herein. However, it will be appreciated that MCP may be used to deposit and pattern other molecules. It will also be appreciated that other soft lithographic techniques may be used to deposit and pattern SAMs and other molecules.

In micro-contact printing (MCP) to form a SAM, the surface relief of PDMS is "inked" with SAM-forming molecules (SFMs), such as alkanethiol, and placed in contact with the surface of a surface, or substrate. The "ink" is transferred to the surface of the substrate and forms a SAM in a pattern that is a projection of the surface relief embossed in the PDMS. Features ranging from 100 nm to 1 mm can be fabricated by MCP.

Soft lithography can be used to create arrays according to the present invention on many types of surfaces. For example, soft lithography can be used to pattern molecules onto rigid or flexible surfaces and onto flat or curved surfaces. Soft lithography can be used to create arrays with high resolution over small surface areas (e.g., one square millimeter) and over large surface areas (e.g., several $cm^3$) and can create features of a range of sizes (e.g., centimeter, millimeter, micrometer, nanometer).

Figure 2:
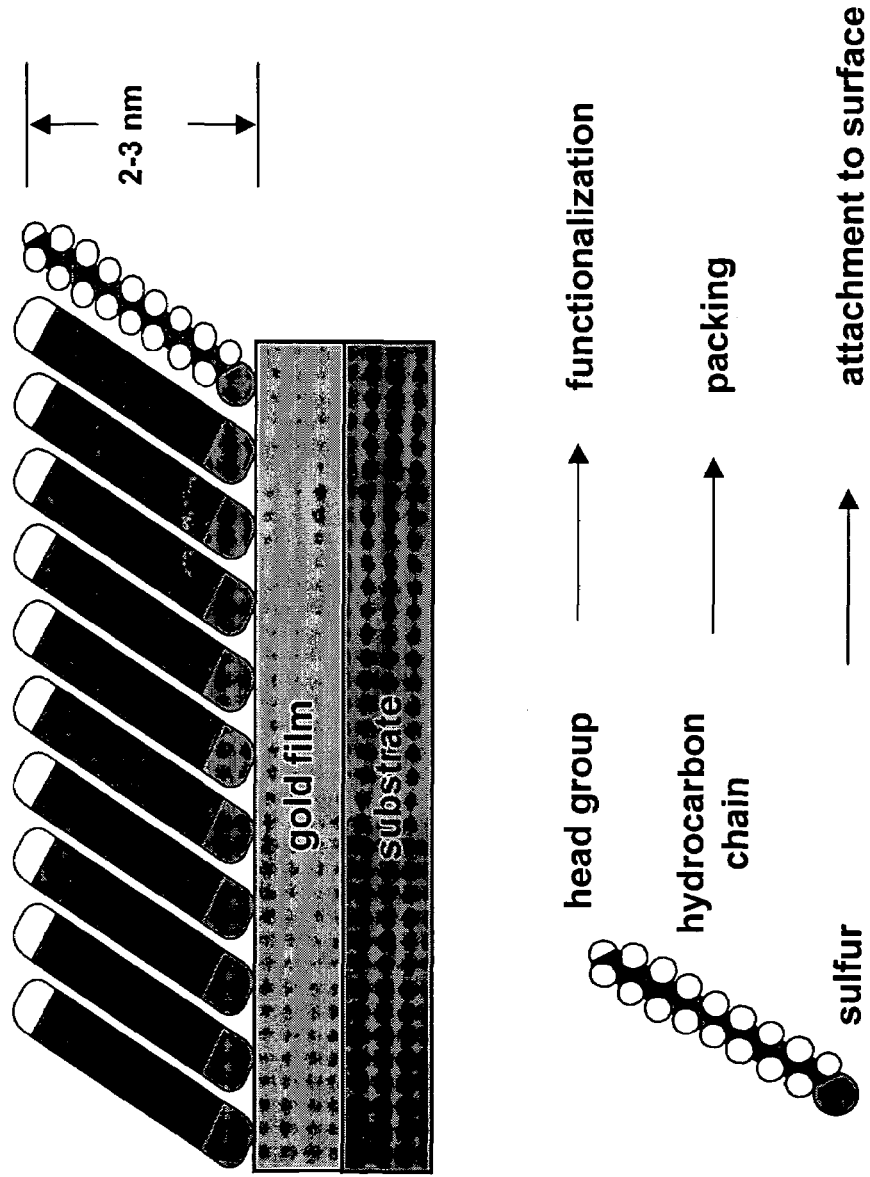
FIG. 2 is a schematic representation of the molecular structure of a Self-Assembled Monolayer (SAM). The functions of portions of the molecules forming the SAM are displayed to the right of the arrows.

The best characterized SAM is that formed by alkanethiols (hydrocarbons with a thiol or —SH group at one end and a functional head group, or X, at the other) on gold. Silver, palladium, platinum, and copper are other examples of surfaces suitable for use with alkanethiol SAMs. These SAMs from via the formation of metal-sulfur bonds between the surface and the thiol, and the subsequent crystalline close-packing of the hydrocarbon chains. Surface engineering arises from the ability to change the chemical and biochemical nature of the head group (X) on the hydrocarbon, which is exposed at the surface. For example, SAMs having the head group of $CF_3$ behave like a Teflon surface, while those having the head group of COOH show wetting characteristics of a glass surface. Methods of soft lithography, including soft lithography using SAMs, are discussed in detail in U.S. Pat. Nos. 5,512,131; 5,620,850; 5,776,748; and 5,976,826, all of which are incorporated herein by reference. See, also, FIGS. 1 and 2.

In certain preferred embodiments, different types of SFMs are arranged in patterns on the surface to form a patterned SAM wherein different portions of the pattern have different binding characteristics. In certain particularly preferred embodiments, the pattern comprises areas or islands of SFMs capable of binding biomolecules. The SFMs comprising a single binding island may have the same specificity and therefore bind the same biomolecules or may have different specificities, so that they bind different biomolecules. Likewise, different islands of SFMs that bind biomolecules may have the same specificity and therefore bind the same biomolecules or may have different specificities, so that they bind different biomolecules.

Preferably, binding islands are surrounded by areas of SFMs that are incapable of binding, or that resist the binding of, biomolecules. Such areas, also called "non-binding areas," are useful because they may reduce or prevent non-specific binding of biomolecules to the array. Non-specific adsorption of biomolecules to the surface can greatly hamper the ability to immobilize specific biomolecules of interest and/or to immobilize biomolecules in specific locations. Such non-binding areas may be created using any suitable method. As a non-limiting example, non-binding areas may be created through the formation of SAMs to which biomolecules do not bind or for which biomolecules have very low affinity.

Such patterning may be achieved through the use of any patterning technique which will produce patterns of the desired size. For example, such patterning may be achieved through the use of soft lithography, washing, or a combination of soft lithography and washing. Where washing is useful, other, similar techniques, such as dripping, spraying, dipping may also be employed. In an example of patterning through soft lithography, SFMs with a first X group ($X_1$) are applied to a suitable surface using a suitable method such as MCP or other soft lithographic technique known in the art. SFMs bearing a second X group ($X_2$) are then applied to the surface in areas not covered by the $X_1$ SFMs using a suitable technique, such as MCP or other soft lithography technique. $X_2$ SFMs may also be applied to surface areas not covered by $X_1$ SFMs by washing the surface with $X_2$ SFMs, which will form SAMs in the areas of the surface not covered by $X_1$ SFMs. Additional SFMs with additional X groups may similarly be applied through such additive process fabrication. Application of SFMs to a surface may also be achieved through washing of the surface with SFMs.

As an example of a useful embodiment, SAM technology may be used to form a SAM at each of 500 spots in a given well of a 96 well plate (or in an area the size of such a well on a substrate) to form 500 binding islands at predetermined locations. If desired, this procedure can be repeated for each of the 96 wells in a 96 well plate (or for each of 96 areas the size and spatial orientation of such wells on a substrate), thereby producing 96 duplicate arrays of 500 different types of binding island each in a predetermined spatial orientation. Similar methods may be used to create arrays of 14,000 binding islands in 384 well plates or on substrates.

In one embodiment, all of the islands of binding SAM comprise the same SFM, i.e., each of the binding islands may be capable of binding to the same type or class of biomolecules. Such an embodiment may be useful, for example, where an arrayer will be used to transfer specific biomolecules to each binding island; here, each binding island may bind any or all of the biomolecules transferred, but mixing of the biomolecules will be prevented because separation is maintained first by the arrayer, then because each type of biomolecule is bound to a predetermined binding island. In another embodiment, different binding islands may comprise SFMs that are specific for different types or classes of biomolecules. Such an embodiment may be especially useful when biomolecules are to be applied to an array of binding islands by washing, such as where the source of the biomolecules is a biological sample which has not been pre-fractionated or pre-differentiated. In other words, such embodiments find particular utility in applications for which it is desired that arrays according to the present invention perform a separation function, as well as an immobilization and localization function (i.e., retaining biomolecules in a predetermined position).

Techniques such as washing, dripping, spraying, dipping, or MCP may be used to surround binding islands with non-binding areas. Biomolecules may then be immobilized on the binding islands using soft lithography, arrayers, or washing, dripping, spraying, dipping. A different type of biomolecule may be immobilized on each of 500 binding islands in a given well of a 96 well plate (or in an area the size of such a well on a substrate) and to predetermine the location of each type of biomolecule in the array of 500 islands. If desired, this procedure can be repeated for each of the 96 wells in a 96 well plate (or for each of 96 areas the size and spatial orientation of such wells on a substrate), thereby producing 96 duplicate arrays of 500 different types of protein each in a predetermined spatial orientation. Similar methods may be used to create arrays of 14,000 types of biomolecules in 384 well plates or on substrates.

X groups that bind biomolecules may be referred to herein as "binding X groups," and SFMs having binding X groups may be referred to herein as "binding SFMs." Likewise, X groups that resist the binding of, or do not bind, biomolecules may be referred to herein as "inert X groups," and SFMs having inert X groups may be referred to herein as "inert SFMs."

A given X group may have a particular specificity when the SFMs are applied to the surface; or SFMs with an X group may be applied, then the X group may be modified or derivatized to alter its binding characteristics. Thus, it will be appreciated that binding SFMs include those SFMs with X groups that are inert or have a binding specificity different from their final desired specificity at the time that they form a SAM, but the binding specificity of which is capable of being altered at some point during the process of making the array of which the SLM forms a part. Likewise, inert SFMs include those SFMs having X groups which bind biomolecules, but are rendered inert at some point during the process of making the array of which the SLM forms a part. Thus, "inert" and "binding" refer to the binding capacity of a SFM after the completion of the production or manufacture of the array of which it forms a part.

In a preferred embodiment, alkanethiol SFMs having a hydrocarbon chain of between 2 and 40 hydrocarbons are used. For SFMs ending in an X group that binds biomolecules, the hydrocarbon chain preferably has 8 to 30 carbon atoms, more preferably has 14 to 18 carbon atoms, and most preferably has 16 carbon atoms. Surfaces which do not bind biomolecules can be formed, for example, using SFMs having three or six ethylene glycol (EG) groups between the hydrocarbon chain and the X group and having a hydroxy (—OH) group or a methyl (—CH$_3$) group as the X group. SFMs which do not bind biomolecules preferably have a hydrocarbon chain of between 3 to 30 carbon atoms, more preferably between 10 to 14 carbon atoms, and most preferably have a hydrocarbon chain of 11 carbon atoms.

In some embodiments, an area composed entirely of binding SFMs will result in the binding of a single biomolecule at more than one site on the biomolecule (i.e., non-specific binding), which often results in denaturation and alteration or destruction of a biomolecule's activities or characteristics. Hence, in a preferred embodiment, a monolayer of biomolecules is immobilized on the surface, and those biomolecules are bound by only one location on the biomolecule, i.e., non-specific binding is avoided.

This objective may be accomplished via the use of both SFMs having X groups which bind to biomolecules ("binding SFMs") and SFMs with X groups that do not bind biomolecules ("inert SFMs") to create a binding island or area comprising binding SFMs that are in close proximity to inert SFMs; this arrangement allows a biomolecule to bind specifically to a binding SFM while preventing non-specific binding of other portions of the biomolecule to other SFMs. Space between binding SFMs may be provided by interspersing binding and inert SFMS. Such interspersing of binding and inert SFMs may be accomplished, e.g., by MCP using a mixture of both binding and inert SFMs as the "ink" to be used in printing the island pattern on the surface. However, the ratio of binding to inert SFMs is important. If the ratio is too high, then the amount of non-specific binding may be too great for detection of the events of interest, depending also on the assay and detection system. If the ratio is too low, then the number of biomolecules bound may be too low for detection of the events of interest, depending also on the assay and detection system. A suitable ratio may be selected for a given assay and detection system using empirical methods. For example, binding islands of varying ratios of binding to inert SFMs, surrounded by areas of inert SAM, may be formed on a surface; biomolecules may be bound to the islands; the surface may be exposed to a solution of biomolecules that bind to or otherwise modify the immobilized biomolecules; the degree of non-specific binding to each island may be measured; and whether the modification is detectable may be determined for each island. Typically, the ratio of binding to inert SFMs may be between approximately 0.1% and approximately 10–20%. In certain embodiments, a ratio of approximately 1–2% may produce very low (substantially no) non specific binding and detectable amounts of modification.

The optimum ratio of binding to inert SFMs may be determined experimentally using the guidance provided herein. Specifically, islands with varying known ratios of SFMs are printed, and biomolecules are allowed to bind. Techniques such as surface plasmon resonance can then be used to analyze the islands. When an island having a complete monolayer of biomolecules and without non-specific binding of biomolecules is located, then it is known that the ratio used to produce the ink for that island is an optimum ratio of binding to inert SFMs. It will appreciated that the optimum ratio will vary from biomolecule to biomolecule and will also vary with the types of SFMs used. It will also be appreciated that, in certain applications, a layer of biomolecules that is, for example, more sparse than a complete monolayer may be desired. In these cases, the above-described method may still be used to determine the ratio of binding to inert SFMs that is optimal for creating the desired conditions.

Islands or areas comprising both binding and inert SFMs and forming an area to which biomolecules bind may be referred to herein as a "binding island" or "binding area."

Biomolecules may be immobilized on SFM X groups using several different systems. As one example, EDS-NHS may be used to create a covalent bond between a biomolecule and a SFM. As another example, SFMs may be produced which end in amine groups, which are coupled to biotin, which is in turn coupled to streptavidin. Biotinylated biomolecules will then bind strongly to the streptavidin on the SFMs. The use of different binding systems facilitates the immobilization of different biomolecules on specific and discreet areas of the surface.

One or more different biomolecules may be immobilized on a single surface. In certain embodiments, many different biomolecules, e.g., 1000's, are immobilized. In other embodiments, fewer different biomolecules, e.g., 50 or fewer, are immobilized.

The biomolecules immobilized on a surface, also referred to as "immobilized biomolecules," to form an array may be any biomolecule sought to be studied. As non-limiting examples, immobilized biomolecules may comprise carbohydrates, nucleic acids, proteins, polypeptides, and lipids. Likewise, the biomolecules to which the immobilized biomolecules are exposed may comprise any biomolecule sought to be studied. These biomolecules, also referred to herein as "biomolecules in solution," may comprise, as non-limiting examples, carbohydrates, nucleic acids, lipids, and/or proteins.

In a particularly preferred embodiment, a SAM comprising a pattern of binding islands is created, wherein the islands comprise an optimum ratio of binding to inert SFMs and the regions between the binding islands comprise inert SFMs, such that biomolecules do not bind to the regions between the binding islands.

In certain embodiments, a single type of biomolecule in solution is exposed to immobilized biomolecules. In other embodiments, the solution to which immobilized biomolecules are exposed comprises more than one type of biomolecule. In certain embodiments the solution to which immobilized biomolecules are exposed comprises biomolecules of more than one class. Biomolecules useful in embodiments of the present invention include both biomolecules whose identity is known and also include both biomolecules whose identity is unknown. Biomolecules useful in embodiments of the present invention include both biomolecules whose function or activity is known and those biomolecules whose function or activity is unknown. Biomolecules whose function or activity is unknown may be referred to herein as "uncharacterized."

Drugs, toxins, and other biomolecules in solution may be a single known biomolecule or a mixture of known biomolecules, i.e. the composition of the solution may be predetermined. Similarly, the activities or characteristics of the biomolecules may be known, or the biomolecules may be uncharacterized. In other embodiments, the composition of the solution may be uncharacterized or unknown, i.e., the biomolecules in solution may be of unknown identity or have unknown activities or functions. In still other embodiments, the composition of the solution to be exposed to immobilized biomolecules may be partially characterized or partially known, e.g., some biomolecules in the solution may be identified and/or characterized, and others may be unidentified and/or uncharacterized. Non-limiting examples of embodiments in which some or all of the biomolecules in a solution may be unidentified and/or uncharacterized include embodiments in which the solution is or is derived from a cell lysate and embodiments in which the solution is or is derived from a library, such as a protein library.

Similarly to the biomolecules in solution, immobilized biomolecules may comprise both identified and unidentified biomolecules and both characterized and uncharacterized biomolecules. In many embodiments, biomolecules which are both known and characterized are immobilized on a surface to form arrays according to the present invention.

In certain embodiments, immobilized biomolecules are chosen which are known to modify or bind to a particular second biomolecule of interest. In such embodiments, immobilized biomolecules can be used to screen for the presence of other biomolecules in solutions, such as cell culture supernatants, cell lysates, physiological fluids, and protein libraries.

In certain embodiments, immobilized biomolecules and biomolecules in solution are selected because the effect of one or more biomolecules in solution on one or more biomolecules immobilized on the surface is sought to be determined. Likewise, biomolecules may be selected to determine the effects of one or more biomolecules immobilized on the surface on one or more biomolecules in solution. Further, the biomolecules may be selected because the interactions between the biomolecules is sought to be elucidated. Such effects and interactions include, but are not limited to, binding of a biomolecule to another biomolecule and activation of, inhibition of, and modification of a biomolecule by another biomolecule. Modifications include, but are not limited to, phosphorylation, dephosphorylation, methylation, acetylation, lipidation, farnesylation, glycosylation, prenylation, ubiquitination, hydroxylation, dehydroxylation, carboxylation, decarboxylation nitrosylation, oxidation, reduction, hydrogenation, and dehydrogenation. Other non-limiting examples of modifications include allosteric transitions, hydrolysis, glycolysis, proteolysis, and metabolic and catabolic alterations. These and other modifications to biomolecules may be investigated using embodiments of the present invention.

Immobilized biomolecules may be derived from any source of interest. In certain embodiments, biomolecules to be immobilized are or are derived from a supernatant of a cell culture. The cells in culture may be derived from any source of interest. In certain other embodiments, biomolecules to be immobilized are or are derived from a cell lysate. The cell lysate may be derived from any source of interest. Non-limiting examples of such sources include cells in culture, immortalized cell lines, and cells, tissues, or organs taken directly from a living or dead organism. In other embodiments, biomolecules to be immobilized are or are derived from a fluid or fluids taken from a living or dead organism. Non-limiting examples of such fluids include blood, tears, saliva, gastrointestinal fluid, amniotic fluid, bone marrow, plasma, lymph, extracellular fluids, sap, cerebrospinal fluid, and urine. Such fluids may be referred to herein as "physiological fluids." In yet other embodiments, biomolecules to be immobilized are or are derived from a target protein library or other library. In certain embodiments, biomolecules to be immobilized comprise drugs or drug candidates. Samples comprising biomolecules other than biomolecules of interest may be fractionated, thereby reducing or eliminating biomolecules not of interest, before being applied to binding islands of the present invention. However, in certain embodiments of the present invention, such fractionation is unnecessary because the binding islands exhibit binding specificity.

In certain embodiments, these biomolecules are proteins. One or more types of proteins may be immobilized on a surface. In certain embodiments, the proteins are immobilized using methods and materials that minimize the denaturing of the proteins, that minimize alterations in the activity of the proteins, or that minimize interactions between the protein and the surface on which they are immobilized. In certain embodiments, these biomolecules are proteins involved in pathways that are important in signal transduction.

Surfaces bearing immobilized biomolecules are exposed to solutions comprising molecules which react with, modify, or are modified by the immobilized biomolecules. Such solutions may be referred to herein as "solutions of interest." In certain embodiments, one or more specific molecules of interest is suspended in a solution. In certain embodiments, the solution is or is derived from a supernatant of a cell culture. The cells in culture may be derived from any source of interest. In certain other embodiments, the solution is or is derived from a cell lysate. The cell lysate may be derived from any source of interest. Non-limiting examples of such sources include cells in culture, immortalized cell lines, and cells, tissues, or organs taken directly from a living or dead organism. In other embodiments, the solution is or is derived from a fluid or fluids taken from a living or dead organism. Non-limiting examples of such fluids include blood, tears, saliva, gastrointestinal fluids, amniotic fluid, plasma, bone marrow, lymph, extracellular fluids, cerebro-spinal fluid, and urine. Such fluids may be referred to herein as "physiological fluids." In yet other embodiments, the solution comprises or is derived from a target library or other library. In certain embodiments, the solution to which arrays according to the present invention are exposed include drugs or drug candidates. Samples comprising biomolecules other than biomolecules of interest may be fractionated, thereby reducing or eliminating biomolecules not of interest, before being applied to binding islands of the present invention. However, in certain embodiments of the present invention, such fractionation is unnecessary because the binding islands exhibit binding specificity.

As used herein, the term "solution" includes any media in which molecules are not bound to a substrate that is fixed in position in relation to biomolecules immobilized on surfaces according to the present invention.

Proteins, drugs, toxins, other biomolecules, cell lines, cells, physiological fluids, and libraries which may be studied using arrays according to the present invention may be derived from sources that include, but are not limited to animals, plants, algae, fungi, bacteria, viruses, protazoa, and any other life form of interest. Arrays according to the present invention are also useful for studying proteins and other biomolecules produced via chemical synthesis, enzymatic synthesis, recombinant nucleotide technology, and other in vitro methods. In embodiments in which the solution is or is derived from a fluid, culture supernatant, library, or cell lysate, the solution may be an entire library or unaltered cell lysate, culture supernatant, or fluid; or the library, lysate, supernatant, or fluid may be subjected to other methods of separation, fractionation, or characterization, to produce a solution to which an array will be exposed.

In certain embodiments, cells are treated with drugs or drug candidates of interest, then the cells are lysed and arrays according to the present invention are exposed to the cell lysate. In other embodiments, cells are cultured in miniaturized microfluidic systems that are integrated with arrays according to the present invention. Products released by and/or lysates of cells so cultured may then be analyzed on arrays integrated with the cell culturing system itself. Cells may be cultured, lysed, and exposed to arrays without needing to relocate the cells.

In certain embodiments, array systems of the present invention are used to study pathways, such as signal transduction pathways, feedback control systems, and intercellular signaling pathways. Non-limiting examples of pathways which may be studied using arrays according to the present invention are described herein. Because many types of biomolecules may be immobilized on a single array and exposed to a solution containing other biomolecules, complex interactions between biomolecules may be studied by detecting changes, or lack thereof, to intermediary or endpoint biomolecules. For example, one particular biomolecule (A) in solution may be activated or inactivated by another biomolecule (B) which is immobilized or in solution. In one example, it is known that proteins A, B, and C comprise part of a pathway. Specifically, it is known that active A activates B and that active C activates A. In an exemplary array according to the present invention, inactive A and inactive B are immobilized (and therefore cannot react with one another), and are exposed to a solution containing active A, active C, and a potential inhibitor of the pathway. If immobilized A is activated by C in solution, it can be deduced that no inhibitor of C is present in the solution. If immobilized B is activated by A in solution, it can be deduced that the solution contains no inhibitor of A. Conversely, if immobilized A is not activated, it can be deduced that the solution contains an inhibitor of C. If immobilized B is not activated, then the solution contains an inhibitor of A. By analyzing the pattern of activation, or lack thereof, it can be determined where in the pathway the potential inhibitor act, if it in fact is an inhibitor of the examined portion of the pathway. The ability to immobilize multiple biomolecules on a single array also facilitates the monitoring of multiple pathways at one time.

In embodiments wherein array systems of the present invention are used to study pathways, one or more biomolecules known or thought to compose part of that pathway are immobilized in an array. In this way, the interactions of a solution of interest with each of the immobilized biomolecules may be investigated simultaneously. In certain of these embodiments, a spatial arrangement, or array, of biomolecules of a particular pathway is repeated more than time on a surface. Preferably, the each individual array is separated from the others by a physical barrier. The interactions of more than one solution of interest with the immobilized biomolecules can then be investigated simultaneously.

In certain embodiments, array systems of the present invention are used to study particular classes of biomolecules. Non-limiting examples of classes of biomolecules which may be studied using arrays according to the present invention are described herein. The class of biomolecules to be studied may be defined as broadly or narrowly as desired for each particular embodiment. As a non-limiting example, many types of kinases may be immobilized as a single array. Because many types of biomolecules may be immobilized on a single array and exposed to a solution containing other biomolecules, the interactions between biomolecules in a particular solution of interest and many types of immobilized biomolecules may be investigated simultaneously.

In embodiments wherein array systems of the present invention are used to study classes of biomolecules, one or more types of biomolecules known or thought to belong to the defined class are plated as a single array. In this way, the interactions of a solution of interest with each of the immobilized biomolecules may be investigated simultaneously. In certain of these embodiments, a spatial arrangement, or array, of biomolecules of a particular pathway is repeated more than time on a surface. Preferably, the each individual array is separated from the others by a physical barrier. The interactions of more than one solution of interest with the immobilized biomolecules can then be investigated simultaneously.

As a non-limiting example, arrays comprising members of a class of biomolecules may be used to investigate the specificity of a drug candidate. For example, if a biomolecule is known to affect a target kinase, and therefore be a good drug candidate, it will be desirable to know whether and how the drug candidate affects other kinases. Identification of drugs that are very specific for their intended targets are useful because the side effects associated with their administration are commonly greatly reduced compared to the side effects associated with less specific drugs.

In certain embodiments wherein the biomolecules of interest are proteins, the array of immobilized biomolecules is exposed to solutions containing enzymes specific to these proteins and potential activators or potential inhibitors of those enzymes. Post-translational modifications of the immobilized substrates by the enzymes in solution are detected by antibodies that are specific to those modifications. By monitoring the turnover of the immobilized proteins, activities of the enzymes in the sample can be determined. These arrays have the advantage that they can detect the presence of enzymes that are present at low concentrations (because the enzymes are catalytic and hence give amplified signals).

By patterning just two biomolecules on an array, twice as much biochemical information can be gained from one experiment; for example, the specificity and efficacy of an inhibitor can be determined in a single experiment rather than a set of experiments. This concept can easily be extended to larger numbers of substrates, e.g., several of the MAPK family such as ERK1 to ERK7, p38, and p57 MAPKs could be patterned on one array. Many signal transduction pathways are interconnected and the array system of the present invention will allow researchers to probe these interconnections in one experiment. These more complex arrays will allow the screening of inhibitors against large numbers of pathways, which will greatly speed up screening: screening against hundreds or thousands of targets on one array means that only one experiment is done rather than hundreds or thousands.

Modifications or binding of biomolecules in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays (SPA); mass spectroscopy, such as MALDI and MALDI-TOF; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "Miniaturized FRET assays and microfluidics: key components for ultra-high-throughput screening," *Drug Discov Today* 4(8):363–369 (1999), and references cited therein; Lakowicz J R, *Principles of Fluorescence Spectroscopy*, 2nd Edition, Plenum Press (1999).

For example, in certain embodiments, antibodies reactive with a biomolecule having a specific modification, but not reactive with non-modified biomolecules or biomolecules having other modifications, are used to detect that specific modification. Binding to one or more antibodies may be assayed. In embodiments in which binding to more than one antibody is assessed in a single assay, different antibodies may be differentially labeled. Labeling of antibodies is well-known in the art. As non-limiting examples, antibodies may be radiolabeled or labeled with fluorescent tags. In other embodiments, mass spectrometry is used to differentiate between modified and non-modified biomolecules.

The ability to confine multiple copies of a single or multiple predetermined types of biomolecules to specific islands provided by the present invention creates many utilities and advantages. For example, more than one immobilized biomolecule may be used in a single assay, without the possibility of interaction between the immobilized biomolecule. As another example, in embodiments wherein the biomolecules changes in which are to be detected are immobilized biomolecules, the ability to know precisely where a given specific biomolecule is located on an array facilitates detection of those changes. For example, the ability to know precisely where a given specific biomolecule is located on an array allows for one detection system to be used to detect more than one effect. For example, there are a considerable, but limited, number of fluorescent dyes available which may be conjugated to antibodies for detection of different biomolecules and for differentiation between them. Thus, only a limited number of antibodies can be used for a singular assay while retaining the ability to distinguish which antibodies have bound to their targets. The array systems of the present invention spatially confine types of immobilized biomolecules. Therefore, a given fluorescent dye can be used to label more than one antibody because antibodies with different specificities labeled with the same dye may be distinguished from one another based on their position in the array. Likewise, when techniques that detect mass changes are employed, knowledge of (1) the placement of each of one or more particular type of biomolecule and (2) which of one or more solutions of interest was exposed to a given type of biomolecule at a given location on an array allows the investigator to attribute a detected change in mass to a particular type of biomolecule exposed to a particular solution of interest.

Arrays comprising binding islands or areas may be included in kits, and such kits comprise another embodiment of the present invention. Such kits may also include, as non-limiting examples, reagents useful for preparing biomolecules for immobilization onto binding islands or areas of an array according to the present invention, reagents useful for detecting modifications to immobilized biomolecules, and reagents useful for detecting binding of biomolecules from solutions of interest to immobilized biomolecules.

Likewise, arrays comprising immobilized biomolecules may be included in kits, and such kits comprise yet another embodiment of the present invention. Such kits may also include, as non-limiting examples, reagents useful for detecting modifications to immobilized biomolecules or for detecting binding of biomolecules from solutions of interest to immobilized biomolecules.

Laboratory instruments and other equipment useful in the practice of the present invention may also be included in kits according to the present invention.

Methods and arrays of the present invention facilitate the simultaneous study of many different molecular interactions. Such simultaneous study confers many advantages, such as, but not limited to, high throughput, ease of automation, and greater comparability between samples due to simultaneous processing. As an example, using methods of the present invention, it is possible to immobilize a different type of biomolecule on each of 500 binding islands in a given well of a 96 well plate (or in an area the size of such a well on a substrate) and to predetermine the location of each type of biomolecule in the array of 500 islands. If desired, this procedure can be repeated for each of the 96 wells in a 96 well plate (or for each of 96 areas the size and spatial orientation of such wells on a substrate), thereby producing 96 duplicate arrays of 500 different types of biomolecule each in a predetermined spatial orientation. In such an embodiment, 500 different types of biomolecule may simultaneously be exposed to 96 different treatments by placing one of 96 different solutions of biomolecules into each of the 96 wells (or onto each of 96 areas the size and spatial orientation of such wells on a substrate).

Techniques such as MCP or arrayers may be used to create a pattern of binding SAMs on a surface. Techniques such as washing, dripping, spraying, dipping, or MCP may be used to surround binding islands with non-binding areas. In one embodiment, all of the islands of binding SAM comprise the same SFM, i.e., each of the binding islands may be capable of binding to the same type or class of biomolecules. Such an embodiment may be useful, for example, where an arrayer will be used to transfer specific biomolecules to each binding island; here, each binding island may bind any or all of the biomolecules transferred, but mixing of the biomolecules will be prevented because separation is maintained first by the arrayer, then because each type of biomolecule is bound to a predetermined binding island. In another embodiment, different binding islands may comprise SFMs that are specific for different types or classes of biomolecules. Such an embodiment may be especially useful when biomolecules are to be applied to an array of binding islands by washing or similar techniques, such as where the source of the biomolecules is a biological sample that has not previously been fractionated or differentiated. In other words, such embodiments find particular utility in applications for which it is desired that arrays according to the present invention perform a separation function, as well as an immobilization and localization function (i.e., retaining biomolecules in a predetermined position).

It will be appreciated that, it certain embodiments, it may be desirable to produce arrays comprising more than one binding island binding or prepared to bind a single type of biomolecule. Likewise, it will be apparent that, in certain embodiments, it may be desirable to produce islands bound to or capable of binding more than one type of biomolecule.

In these embodiments, as well as in certain other embodiments of the present invention, a large number of biomolecules (approximately 500) can be simultaneously exposed to 96 different solutions comprising different environmental conditions and mixtures of other biomolecules. The effects of each of the 96 solutions on the each of the 500 biomolecules may be evaluated using techniques described herein. The production of arrays, exposure of arrays to solutions of interest, and the measurement or observation of affects of solutions and immobilized biomolecules on one another are all processes which are amenable to high throughput and automation.

The array systems of the present invention have applications in drug discovery, including primary and secondary screening and target validation. The ability to monitor several protein-protein interactions on one array means that a drug candidate can be screened against several potential targets in a signal transduction pathway. Drug-drug interactions, and their effects on cells, biological pathways, and biomolecules may also be investigated using methods and arrays according to the present invention. Counter assays, of the type needed in drug discovery to check the specificity of a hit from a primary screen, can also be included on arrays according to the present invention. The multiplexed nature of arrays according to the present invention would, therefore, reduce the screening time during drug discovery and speed the development of therapeutics. A array based on kinases for screening inhibitors has use in diagnostics in cancer and other diseases, for example, and also in agricultural biotechnology (AgBio). Arrays according to the present invention are also useful in diagnostics.

Arrays according to the present invention also find great use in the life science research market as a tool for studying biological pathways. Non-limiting examples of pathways which may be investigated using methods and arrays according to the present invention include growth/proliferation/differentiation/oncogenic pathways, such as src pathways, integrin scaffold/FAK activated pathways, and Mitogen Activated Protein Kinase (MAPK) cascades. Examples of MAPK cascades include Ras/Raf/MEK/ERK, PKC/Raf/MEK/ERK, G-Protein Coupled Receptors Signaling to MAPK, p38 MAPK, and SAPK/JNK pathways. Other non-limiting examples of pathways which may be investigated using methods and arrays according to the present invention include apoptotic pathways, such as the caspase signaling pathway and p53 pathways; antiapoptotic pathways, such as PI3K/Akt/BAD pathways and Bcl-2 pathways; translational control pathways, such as pathways regulating eIF-2, eIF-4, and p70 S6 kinase; Wnt signaling pathways; and PKC pathways. Further non-limiting examples of pathways which may be investigated using methods and arrays according to the present invention include phospholipid (diacylglycerol/IP3) and Ca2+ regulated signaling pathways, such as PKC activated MAPK, PKC activation of transcription factor NF-κB, and Ca2+/calmodulin activated systems such as CaM kinase II family pathways; cAMP mediated pathways, e.g., regulation of glycogen metabolism by PKA, PKA/CREB; and cGMP mediated pathways. Still other non-limiting examples of pathways which may be investigated using methods and arrays according to the present invention include cell cycle/checkpoint control pathways, such as Cylin Dependent Kinase (CDK) pathways, G1/S Checkpoint pathways (such as CDK4/6-cyclin D, CDK2-cyclin E and Rb), and G2/M DNA Damage Checkpoint pathways (such as cdc2-cyclin B kinase); death receptor signaling pathways, such as Fas/TNFR activated Caspase pathways; pathways associated with mitochondrial control of apoptosis; cytokine activated pathways; pathways associated with chemotaxis; growth factor activated pathways; and ion channel, G-protein coupled receptors, and receptor tyrosine kinases (RTK) activated pathways. Stress activated pathways, such as p38 MAPK pathways activated by environmental stresses and inflammatory cytokines; and SAPK/JNK signaling cascades activated by environmental stresses, inflammatory cytokines, growth factors, and GPCR agonists, including those activated by Rho family (Rac, Rho, Cdc42) and activation of factors such as c-jun, ATF2, and p53, may also be investigated using methods and arrays according to the present invention. Yet other non-limiting examples of pathways which may be investigated using methods and arrays according to the present invention include Jak/STAT signaling pathways, such as IL-6 receptor family pathways; IL-2 receptor pathways; TGF-β superfamily signaling pathways; cytoskeleton pathways, such as Rho sub family (Rho, Rac, cdc42) regulation of actin reorganization; coagulation pathways; respiratory pathways; synthetic pathways, such as protein synthesis, carbohydrate synthesis, fat synthesis, lipid synthesis, and steroid synthesis pathways; metabolic pathways, such as glucose synthesis pathways, glycogen production pathways, and insulin-dependent pathways; catabolic pathways; pathways associated with electron transport; pathways associated with the complement cascade; immune response pathways, including inflammation pathways; allergy triggering pathways; development pathways; and cell differentiation pathways.

Non-limiting examples of types of biomolecules which may be investigated using methods and arrays according to the present invention include proteins, polypeptides, carbohydrates, lipids, polynucleotides, small molecules, and steroids, and modified forms or derivatives thereof. Non-limiting examples of classes of proteins which may be investigated using methods and arrays according to the present invention include enzymes, such as kinases, phosphatases, flipases, esterases, oxidoreductases, transferases, hydrolases, lyases, isomerases, ligases, lipasesglycosyl transferases, glycosidases, synthases, hydrogenases, dehydrogenases, carboxylases, decarboxylases, proteases, glycosyl transferases, glycosidases, farnesyl transferases, isopeptidases, and enzymes that perform: methylation, demethylation, acetylation, deacetylation, lipidation, delipidation, prenylation, deprenylation, ubiquitination, deubiquitination, hydroxylation, dehydroxylation, nitrosylation, denitrosylation, allosteric transitions, hydrolysis, glycolysis, electron transport, respiration, processing of xenobiotics, and metabolic and catabolic alterations; receptors, transcription factors, structural proteins, and derivatives thereof (such as, but not limited to, glycoproteins, glycolipids).

The array systems of the present invention can also be used to study other biological processes such as metabolism of xenobiotics. For example, an array composed of isozymes of cytochrome P450 can be used for in vitro ADME-tox studies and can thereby lead to a reduction in the number of compounds that enter expensive in vivo ADME-tox studies. Arrays according to the present invention can also be used in ADME absorption, distribution, metabolism, and excretion studies.

All publications, patents, and patent applications referenced herein are hereby incorporated by reference to the same extent as if each was individually so incorporated.

Having thus described the invention with reference to certain preferred embodiments, other embodiments will become apparent to one skilled in the art from consideration of the specification and examples. It is intended that the specification, including the examples, is considered exemplary only.

EXAMPLES

Example 1

Figure 4:
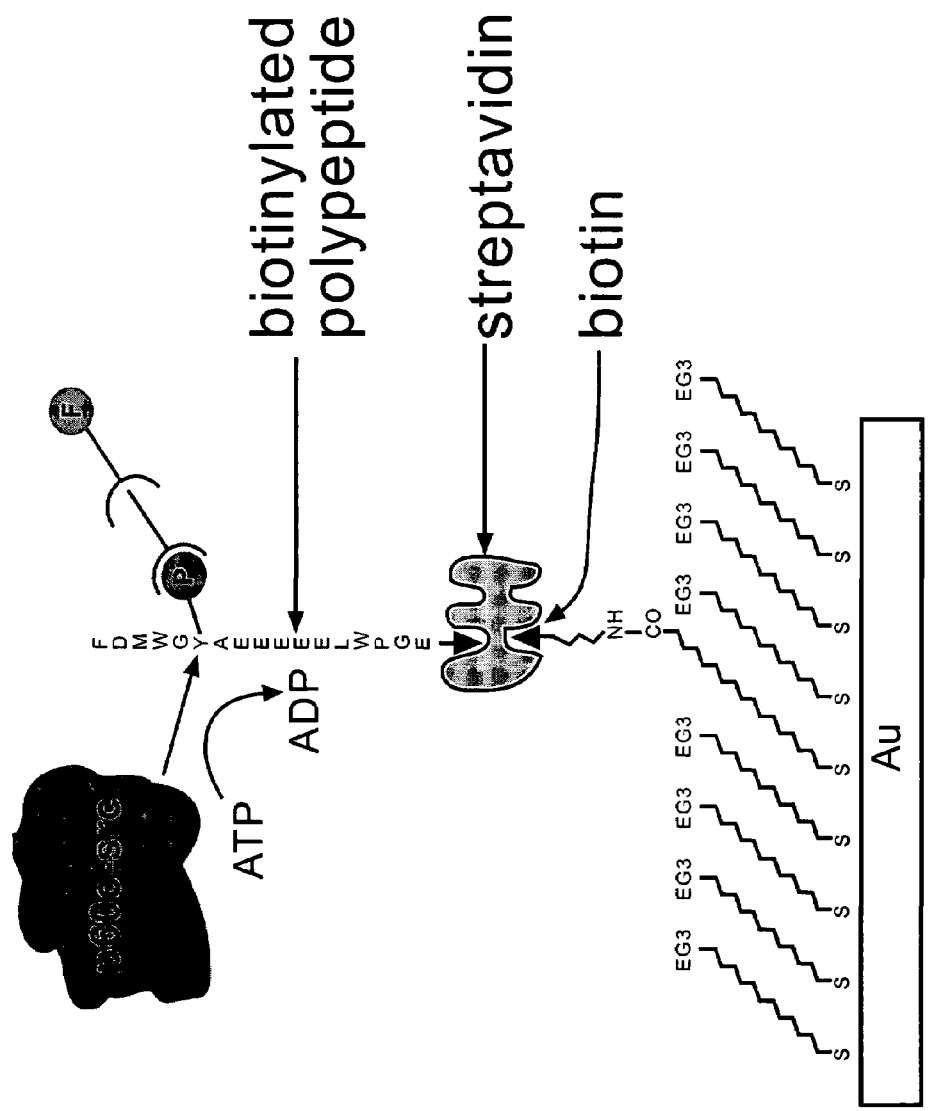
FIG. 4 is a schematic showing an example of a method for immobilizing a peptide substrate biomolecule to a surface for use in an array.

An array of biotinylated-peptide tyrosine kinase substrate was immobilized on a surface that had been micro-contact printed with COOH-terminated thiol (in a background of EG3-terminated thiol) using EDC/NHS coupling, biotin-amine, and streptavidin. See, FIG. 4. A solution containing p60c-src (a member of the src family of kinases) and ATP was then placed on the array to enzymatically add a phosphate group to the tyrosine residue of the substrate. A primary antibody that specifically binds to tyrosine phosphate groups was then incubated on the array. A fluorescein-labeled secondary antibody that recognizes the primary antibody was then incubated on the array. The fluorescence from the bound secondary antibody was then detected using a fluorescence microscope with a fluorescein cube (excitation 480 nm; emission 530 nm).

Figure 5:
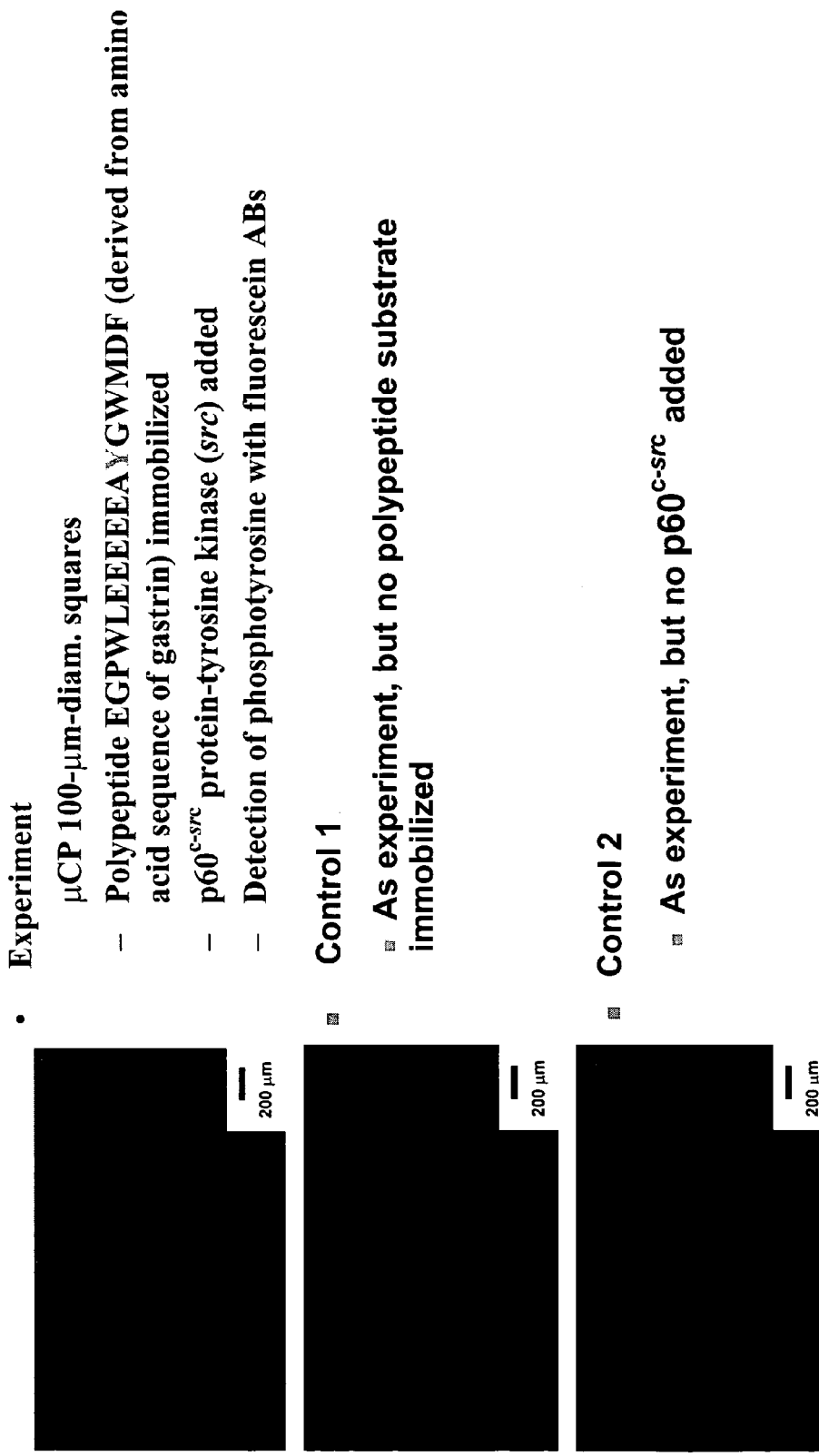
FIG. 5 depicts results obtained from an assay using the array of immobilized peptides depicted in FIG. 4.

The experiment and three control experiments (without enzyme; without substrate; with CH3-terminated microcontact printed SAM) showed that the enzymatic addition of the phosphate group by the kinase could be monitored on the array. The results are shown in FIG. 5.

Example 2

A number of peptides (ranging from 10 to 1000s) that are designed to be substrates for kinases are arrayed onto a surface having islands of binding SAM using a suitable robotic liquid delivery method. Several arrays of the set of peptides are created to yield an "array-of-arrays". After immobilization of the peptides to the surfaces, the surface is washed. Solutions containing a kinase, or a lysate of a cell expressing a certain set of kinases, ATP, salts, and buffer are then placed in contact with the pre-formed peptide arrays. If multiple different solutions or lysates are tested, then each solution is delivered to individual arrays within the "array-of-arrays".

The phosphorylation of the immobilized peptides by the kinase(s) is allowed to proceed (typically at 37° C. for 30 min). The substrate is then washed in a 8 mM solution of sodium dodecyl sulfate (SDS) and tris-buffered saline buffer containing 0.01% Tween-20 surfactant. The degree of phosphorylation of the peptides is then detected using anti-phospho specific antibodies and a secondary antibody that yields a colored or fluorescent product upon development.

Figure 6:
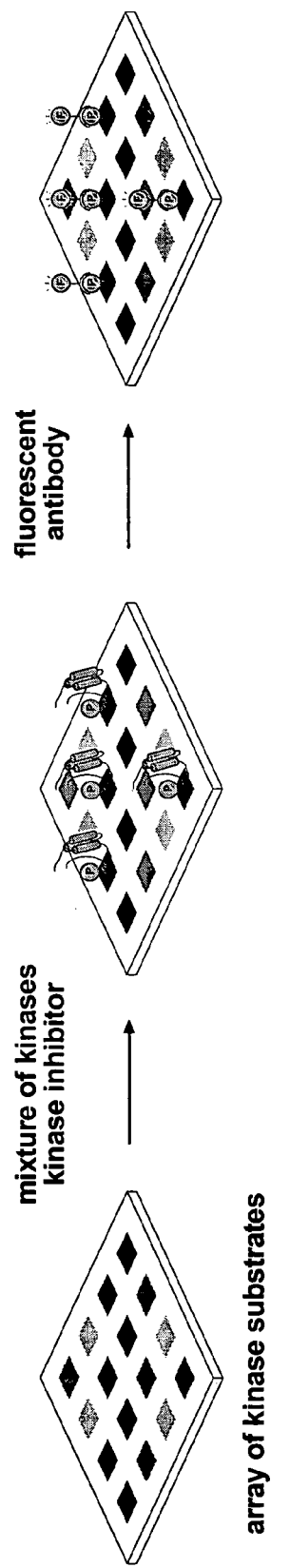
FIG. 6 is a drawing of a multiplexed biomolecule array of immobilized kinase substrates, which would be used for analyzing pathways. As shown in the drawing, a mixture of kinases and kinase inhibitors is added. Which substrates were phosphorylated may be determined after incubation of the array with fluorescently labeled antibodies against phosphorylated substrates.

A calorimetric or fluorescent scanner is then used to quantify the degree of phosphorylation within each element of the arrays. These data provide a phosphorylation "fingerprint" that can be deconvoluted to yield the activity of specific kinases within the test sample for which the arrayed peptides have known activity towards. This method therefore provides a way to determine the activity of kinases within individual pathways direct from the cell lysates. Inhibitors of kinases may also be studied. See. FIG. 6.

Example 3

Figure 3:
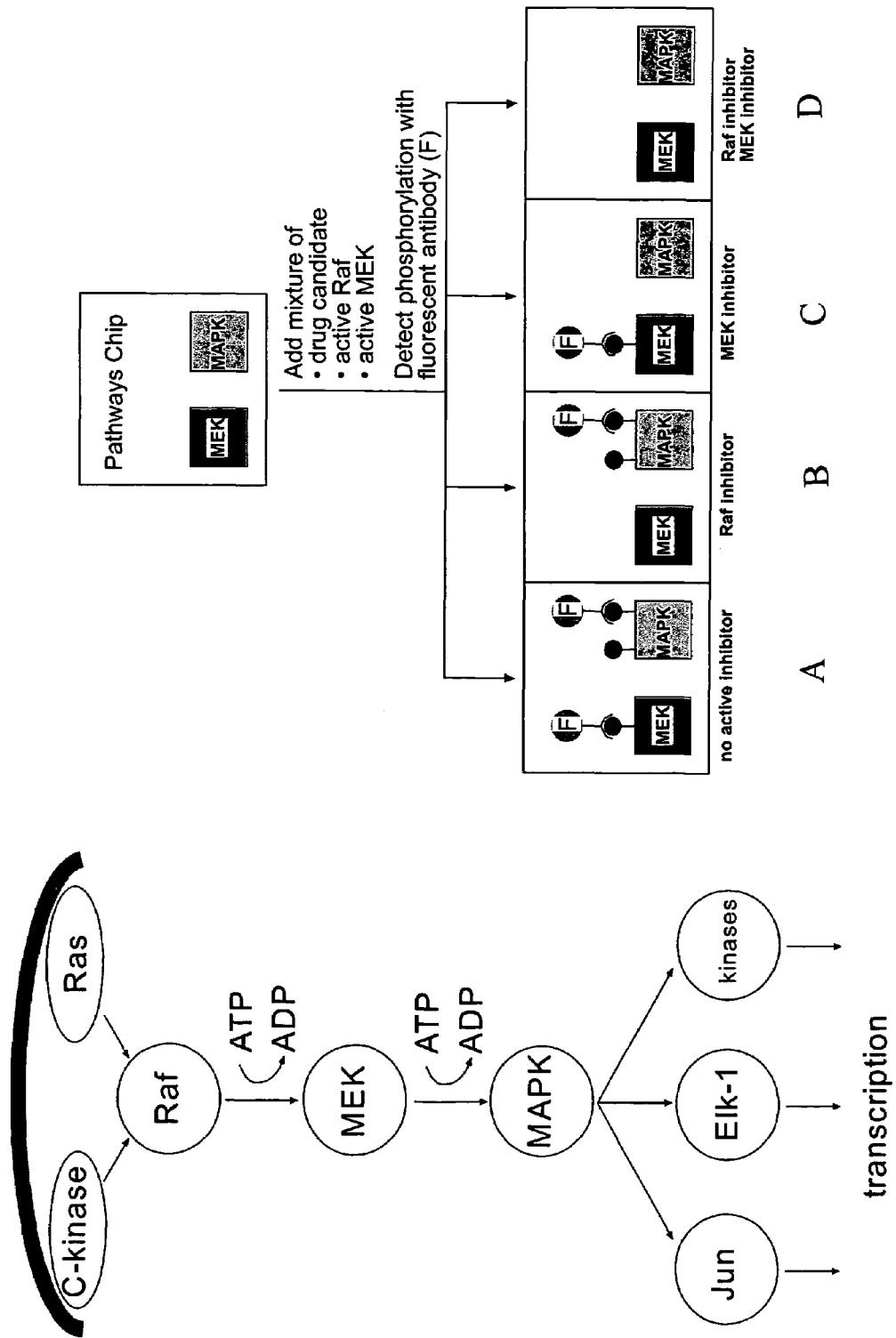
FIG. 3 includes a schematic representation of the Raf/MEK/MAPK pathway (left) and an array according to the present invention (right), which may be used to analyze inhibitors of the pathway.

An array according to the present invention will be used to monitor the Raf/MEK/MAPK pathway. This serine/threonine phosphorylation cascade activates MAP-kinase (MAPK) that initiates proliferation and differentiation. The pathway is schematically illustrated in FIG. 3. Inhibitors of this pathway are being developed as anti-tumor and anti-inflammatory agents. In this array, two proteins involved in the pathway are immobilized on the surface: inactive MEK and inactive MAPK. The solution above the protein array contains the active Raf and MEK enzymes, as well as potential inhibitors of this pathway and ATP. The array is exposed to potential inhibitors of Raf and/or MEK in solution. After incubation of the assay solution above the array, antibodies that are specific to phosphorylated residues of MEK and MAPk are incubated on the array. If the inhibitor prevents the phosphorylation of the immobilized enzymes by RAF or MEK then the antibody will not bind and, therefore, will not be detected after washing. Depending on the specificity and efficacy of the inhibitor, different fluorescent spots will light up.

In FIG. 3, four arrays comprising immobilized MEK and MAPK are each exposed to one of four solutions (A, B, C, and D) comprising different potential inhibitors of MEK and/or Raf. Based on the phosphorylation pattern observed, it can be determined that solution A comprises active inhibitors of neither Raf nor MEK; solution B comprises an inhibitor of Raf, but no inhibitor of MEK; solution C comprises an inhibitor of MEK, but no inhibitor of Raf; and solution D comprises inhibitors of both Raf and MEK.

Example 4

A number of antibodies (typically more than 100) that bind specifically to individual phosphorylated members of a signal transduction pathway are arrayed onto a surface using a suitable robotic liquid delivery method. For example, a set of antibodies including anti-phospho-MAPK, anti-phospho-MEK, and anti-phospho-MEKK, are arrayed onto a surface. A cell lysate, for which a signal transduction cascade had been activated or a certain gene knocked-out, is then exposed to the array of antibodies. After incubation, the degree of binding to the antibody array is then read out by a suitable detection method such as SPR or ELISA. The amount of binding of phosphor-proteins to the corresponding antibodies indicates the degree of activity of individual members of a signal transduction cascade.

Example 5

A reactive SAM is coated in a solution containing a peptide that is a substrate for a particular enzyme. After an incubation time during which the peptide is immobilized, the surface is washed. One or several cell lysates are then incubated with the surface with ATP, salts, and buffer. The degree of phosphorylation of the peptide is then monitored using a phospho-specific antibody and the activity of kinases in the cell lysate can therefore be quantified.

We claim:

1. A method for detecting modification of MEK proteins or MAPK proteins of a Raf/MEK/MAPK pathway, comprising the steps of:
    a) placing a polymer gel contact mask having holes on a substrate, the holes together with the portions of the substrate which overlie the holes forming cavities;
    b) immobilizing inactive MEK proteins and inactive MAPK proteins on areas of the substrate underlying the holes of the polymer gel contact mask that have the size and orientation of wells of a 96 well, 384 well, 1536 well, or 3456 well microwell plate;
    c) exposing the inactive MEK proteins and inactive MAPK proteins to a solution of active Raf proteins, active MEK proteins, ATP, and potential inhibitors of at least one of the active Raf proteins or the active MEK proteins;
    d) allowing binding of the active Raf proteins and the active MEK proteins to the inactive MEK proteins and the inactive MAPK proteins; and
    e) detecting modification of the inactive MEK proteins or the inactive MAPK proteins of the Raf/MEK/MAPK pathway.

2. The method of claim 1, wherein detecting modification comprises the additional step of quantifying the amount present of the inactive MEK or inactive MAPK proteins of the Raf/MEK/MAPK pathway based on the modification thereof.

3. The method of claim 1, wherein detecting modification comprises the additional step of qualitatively or quantitatively determining the level of activity of the inactive MEK or inactive MAPK proteins of the Raf/MEK/MAPK pathway based on the modification thereof.

4. The method of claim 1, wherein detecting the modification comprises the additional step of identifying the affinity or avidity of the inactive MEK or inactive MAPK proteins of the Raf/MEK/MAPK pathway based on the modification thereof.

5. The method of claim 1, further comprising removing the polymer gel contact mask from the substrate before exposing the inactive MEK proteins and inactive MAPK proteins to the solution of active Raf proteins, active MEK proteins, ATP, and potential inhibitors of at least one of the active Raf proteins or the active MEK proteins.

6. The method of claim 1, wherein immobilizing the inactive MEK proteins and inactive MAPK proteins on areas of the substrate comprises forming a self-assembled monolayer on the substrate and binding the inactive MEK proteins and inactive MAPK proteins to the self-assembled monolayer.

* * * * *